United States Patent
Honda et al.

(10) Patent No.: US 8,329,473 B2
(45) Date of Patent: Dec. 11, 2012

(54) METHOD FOR EXTRACTING POLYCHLORINATED BIPHENYLS

(75) Inventors: Katsuhisa Honda, Matsuyama (JP); Tomofumi Takahashi, Matsuyama (JP)

(73) Assignees: Ehime University, Matsuyama-Shi, Ehime (JP); Miura Co., Ltd., Matsuyama-Shi, Ehime (JP)

( * ) Notice: Subject to any disclaimer, the term of this patent is extended or adjusted under 35 U.S.C. 154(b) by 357 days.

(21) Appl. No.: 12/593,483

(22) PCT Filed: Mar. 21, 2008

(86) PCT No.: PCT/JP2008/056004
§ 371 (c)(1), (2), (4) Date: Sep. 28, 2009

(87) PCT Pub. No.: WO2008/123393
PCT Pub. Date: Oct. 16, 2008

(65) Prior Publication Data
US 2010/0116023 A1    May 13, 2010

(30) Foreign Application Priority Data
Mar. 29, 2007 (JP) .................. 2007-089876
Sep. 18, 2007 (JP) .................. 2007-240424

(51) Int. Cl.
*G01N 30/02* (2006.01)
(52) U.S. Cl. ........ 436/161; 436/177; 436/178; 210/656; 210/660; 210/690; 210/691
(58) Field of Classification Search ............. 436/124, 436/126, 140, 161, 174, 177, 178; 210/633, 210/656, 660, 690, 691; 73/61.53, 61.52
See application file for complete search history.

(56) References Cited

U.S. PATENT DOCUMENTS
2005/0194318 A1* 9/2005 Ozbal et al. .......... 210/656
(Continued)

FOREIGN PATENT DOCUMENTS
JP    61-68119 A    4/1986
(Continued)

OTHER PUBLICATIONS
Fujita et al. Journal of Environmental Chemistry vol. 15 No. 1 pp. 117-128 2005.*
(Continued)

*Primary Examiner* — Yelena G Gakh
*Assistant Examiner* — Christopher A Hixson
(74) *Attorney, Agent, or Firm* — Birch, Stewart, Kolasch & Birch, LLP

(57) ABSTRACT

Column which includes a first column with an upper layer of $H_2SO_4$ silica gel and a lower layer $AgNO_3$ silica gel and a second column packed with alumina, connected detachably to a lower end of the first column. An oily liquid containing polychlorinated biphenyls, is added to the upper layer and heated. An aliphatic hydrocarbon solvent is supplied to the upper layer, whereby polychlorinated biphenyls captured by the first column are dissolved in the aliphatic hydrocarbon and then flow to the second column. The polychlorinated biphenyls are captured by the alumina which is located near the inlet of the second column, which is then detached from the first column. A hydrophobic solvent is passed through the second column in a direction opposite to the direction in which the aliphatic hydrocarbon was passed, providing an extract containing the polychlorinated biphenyls dissolved in a small amount of the hydrophobic solvent.

14 Claims, 13 Drawing Sheets

U.S. PATENT DOCUMENTS

| | | | |
|---|---|---|---|
| 2006/0076270 A1* | 4/2006 | Poshusta et al. | 208/208 R |
| 2006/0281961 A1* | 12/2006 | Prasad | 588/300 |
| 2009/0107213 A1 | 4/2009 | Honda et al. | |

FOREIGN PATENT DOCUMENTS

| | | | |
|---|---|---|---|
| JP | 2000-28598 A | 1/2000 | |
| JP | 2000-88825 A | 3/2000 | |
| JP | 2001-330598 A | 11/2001 | |
| JP | 2002-365273 A | 12/2002 | |
| JP | 2003-107062 A | 4/2003 | |
| JP | 2003-114222 A | 4/2003 | |
| JP | 2005-140522 A | 6/2005 | |
| JP | 2006-47044 A | 2/2006 | |
| WO | WO 2006/132027 A1 | 12/2006 | |

OTHER PUBLICATIONS

Machine Translation of JP 2002-365273 obtained from the Patent Abstracts of Japan website by the examiner on Nov. 16, 2011.*

Takeshi, Nishiguchi et al. "Dehydration of alcohols catalyzed by copper(II) sulfate adsorbed on silica gel." Tetrahedron Letters (1987) 28 4565-4568.*

Nobuyoshi, Yamashita et al. "Concentrations and profiles of polychlorinated naphthalene congeners in 18 technical polychlorinated biphenyl preparations." Environ. Sci. Technol. (2000) 34 4236-4241.*

"Method for Determination of Dioxins in Stationary Source Emissions", Japanese Industrial Standard, 2005, pp. 1-76, JIS K 0311, Tokyo, Japan.

"Method of Testing Standards Concerned with General Waste Subject to Special Control and Industrial Waste Subject to Special Control", Ministry of Health and Welfare of Japan, Appendix No. 2 in Announcement No. 192, 1992.

"Temporary Manual for Examination of Exogenous Endocrine-Disrupting Chemicals", Environmental Agency of Japan, Oct. 1998, pp. I-1 thu I-16.

"Testing Methods for Polychlorinated Biphenyl (PCB) in Industrial Water and Waste Water", Japanese Industrial Standard, Mar. 25, 2006, pp. 1-17, JIS K 0093, Japan.

Hiroyuki Fujita et al., "Investigation of Purification Method by Heating Multilayer Silica Gel Column in Dioxins Analysis", Journal of Environmental Chemistry, Mar. 25, 2005, vol. 15, No. 1, pp. 117-128.

Hiroyuki Fujita et al., "Investigation of the Purification/Concentration Method for Dioxins Analysis by GC-MS and Bioassay", Journal of Environmental Chemistry, Sep. 22, 2005, vol. 15, No. 3, pp. 585-596.

Nondek L., et al., LC Clean-up and GC/MS Analysis of Polycyclic Aromatic Hydrocarbons in River Sediment, Chromatographia, Sep. 1993, vol. 37, No. 7/8, pp. 381-386.

Supplementary European Search Report of Aug. 7, 2012 in application EP 08 73 9128.0.

Grochowalski et al., Carbon Column as a Clean-up Method for Oily Samples Purification for the Determination of Polychlorinated Dibenzodioxins (PCDDs) and Polychlorinated Dibenzofurans (PCDFs), Chem. Anal. (Warsaw), vol. 43, 1998, pp. 399-408.

Hess et al., "Critical review of the analysis of non- and mono-ortho-chlorobiphenyls", Journal of Chromatography A., vol. 703, 1995, pp. 417-465.

* cited by examiner

METHOD FOR EXTRACTING POLYCHLORINATED BIPHENYLS

TECHNICAL FIELD

The present invention relates to a method for extracting polychlorinated biphenyls and in particular to a method for extracting polychlorinated biphenyls from a polychlorinated biphenyl-containing oily liquid.

BACKGROUND ART

As electric insulating oils for electric instruments such as transformers and capacitors, those consisting of mineral oils containing polychlorinated biphenyls (referred to hereinafter as "PCBs") excellent in electrical insulation properties were generally used. However, the toxicity of PCBs to the living body has been confirmed, so that in Japan, the production and import of PCBs have already been prohibited, and use of electric insulating oils containing PCBs came to be substantially prohibited. PCBs-containing electric insulating oils and the like used in the past might cause environmental pollution during their disposal process and have thus been stored as they are until now for a long time by manufacturers of electric instruments, enterprises using such oils, and industrial waste disposers.

Meanwhile, with the background of establishment of safe chemical decomposition methods of PCBs, the PCB Special Measures Law was enacted in 2001 in Japan, and this law required that all PCBs wastes including PCBs-containing electric insulating oils which had been used or stored, be disposed of by July, 2016.

It was initially assumed that PCBs wastes that should be disposed of under the PCB Special Measures Law were limited to those electric insulating oils and the like which had been manufactured or used until production and use of PCBs were prohibited and which had been stored heretofore. However, there were cases where PCBs estimated to be mixed during the production process were detected in electric insulating oils and the like manufactured after prohibition of use of PCBs, and thus some electric insulating oils used at present in electric instruments such as transformers may correspond to PCBs wastes subject to the PCB Special Measures Law. The PCB Special Measures Law set out the time limit as described above, so there has been demand for promptly judging whether electric insulating oils used in existing electric instruments and the like correspond to the PCBs wastes subject to the PCB Special Measures Law (that is, oils and the like containing PCBs at a concentration of not less than 0.5 mg/kg correspond to the PCBs wastes subject to the PCB Special Measures Law, and judgment of whether oils and the like correspond to the PCBs wastes or not is referred to as PCB screening).

Whether samples collected from objects such as electric insulating oils contain PCBs at a predetermined concentration is judged usually on the basis of analysis results by highly sensitive analyzers such as gas chromatography-mass spectrometry (GC-MS) and gas chromatography-electron capture detection (GC/ECD), for which the samples should be subjected to advanced pretreatment to remove interfering components which can affect analysis results. Such pretreatment is carried out in accordance with the method described in Appendix No. 2 in Announcement No. 192 issued in 1992 by the Ministry of Health and Welfare of Japan "Method of Testing Standards Concerned with General Waste Subject to Special Control and Industrial Waste Subject to Special Control" (referred to hereinafter as an "official method"). However, the official method requires many steps of complicated treatments such as dimethylsulfoxide (DMSO)/hexane partition, sulfuric acid treatment, alkali treatment and silica gel column treatment, thus requiring a long time by day until completion and costing very high to be performed.

However, it is estimated that about 6 million electric instruments such as transformers are in use in Japan, so that when all electric insulating oils in these electric instruments are to be pretreated and analyzed by the official method, huge amounts of time and cost are required. Accordingly, it is substantially difficult under present circumstances to subject electric insulating oils in all electric instruments to PCB screening until the time limit stipulated under the PCB Special Measures Law.

Accordingly, a method for pretreating the objects has been examined as a substitute for the official method. For example, JP 2003-114222 A (particularly, paragraph numbers 0004 and 0007) describes a pretreatment method in accordance with the method stipulated in JIS K 0311 "Method for Determination of Dioxins in Stationary Source Emissions". In this pretreatment method, organic components in a sample collected from an object to be judged are extracted with an organic solvent to prepare an extract, and this extract is passed through a silica gel column and an alumina column in this order in chromatography. On this occasion, part of impurity components other than PCBs contained in the extract is decomposed during passage through the silica gel column, and the resultant decomposition product is captured by the silica gel column. Then, when a developing solvent passed through the alumina column is collected, a solution of PCBs (that is, a solution of PCBs in the developing solvent) from which impurity components are removed is obtained, and this solution can be used as an analytical sample.

However, the substitute method described above is troublesome in preparing an extract from a sample of an object to be judged, the time necessary for treatment still remains so long as about 2 to 3 days, and the cost for pretreatment is high. Accordingly, the substitute method is substantially meaningless at least as a pretreatment method for PCB screening, which is substituted for the official method.

An object of the present invention is to enable PCBs to be extracted by an easy operation in a shorter time from an oily liquid such as an electric insulating oil containing PCBs.

DISCLOSURE OF THE INVENTION

The present invention relates to a method for extracting polychlorinated biphenyls from a polychlorinated biphenyls-containing oily liquid. This extraction method includes the steps of: adding an oily liquid to a sulfuric acid silica gel layer, allowing the sulfuric acid silica gel layer to which the oily liquid is added to be kept in a state heated to at least 35° C. for a predetermined time and then cooling the layer to ordinary temperature, supplying an aliphatic hydrocarbon solvent to the sulfuric acid silica gel layer cooled to ordinary temperature, allowing the aliphatic hydrocarbon solvent passed through the sulfuric acid silica gel layer to be supplied to, and passed through, a silver nitrate silica gel layer, allowing the aliphatic hydrocarbon solvent passed through the silver nitrate silica gel layer to be supplied to, and passed through, an alumina layer, allowing a hydrophobic solvent capable of dissolving polychlorinated biphenyls to be supplied to, and passed through, the alumina layer, and securing the hydrophobic solvent passed through the alumina layer.

In this extraction method, when the sulfuric acid silica gel layer to which an oily liquid is added is kept in a state heated to at least 35° C. for a predetermined time, impurity components, which are mainly aromatic compounds, other than polychlorinated biphenyls contained in the oily liquid are rapidly decomposed by reaction with the sulfuric acid silica gel layer. The resultant decomposition products, together with polychlorinated biphenyls, are retained in the sulfuric acid silica gel layer. Then, when the sulfuric acid silica gel layer cooled to ordinary temperature is supplied with an aliphatic hydrocarbon solvent, the aliphatic hydrocarbon solvent is passed through the sulfuric acid silica gel layer and supplied to a silver nitrate silica gel layer, and then passed through the silver nitrate silica gel layer. On this occasion, the polychlorinated biphenyls and a part of the decomposition products retained in the sulfuric acid silica gel layer are dissolved in the aliphatic hydrocarbon solvent supplied to the sulfuric acid silica gel layer and are supplied from the sulfuric acid silica gel layer to the silver nitrate silica gel layer. Then, a part of the decomposition products contained in the aliphatic hydrocarbon solvent supplied to the silver nitrate silica gel layer is adsorbed by, and retained in, the silver nitrate silica gel layer. The polychlorinated biphenyls contained in the aliphatic hydrocarbon solvent supplied to the silver nitrate silica gel layer remain dissolved in the aliphatic hydrocarbon solvent and are passed through the silver nitrate silica gel layer.

Next, when the aliphatic hydrocarbon solvent passed through the silver nitrate silica gel layer, that is, the aliphatic hydrocarbon solvent in which the polychlorinated biphenyls are dissolved, is supplied to and passed through the alumina layer, the polychlorinated biphenyls dissolved in the aliphatic hydrocarbon solvent are captured by the alumina layer, while impurity components (mainly paraffins when the oily liquid is an electric insulating oil consisting of mineral oils) other than polychlorinated biphenyls, remaining in the aliphatic hydrocarbon solvent, are not captured by the alumina layer but passed together with the aliphatic hydrocarbon solvent through the alumina layer. Then, when a hydrophobic solvent is supplied to and passed through the alumina layer through which the aliphatic hydrocarbon solvent is passed, the polychlorinated biphenyls captured by the alumina layer are dissolved in the hydrophobic solvent, extracted from the alumina layer and secured as a solution in the hydrophobic solvent.

According to this extraction method, therefore, polychlorinated biphenyls can be extracted from a polychlorinated biphenyls-containing oily liquid in a shorter time by an easy operation.

In this extraction method, the sulfuric acid silica gel layer, the silver nitrate silica gel layer and the alumina layer used are not particularly limited in form for use, and may be used by packing them in a column or disposing them in a suitable strainer but usually are preferably used by packing them in a column. Columns packed with the sulfuric acid silica gel layer, the silver nitrate silica gel layer and the alumina layer are preferably a first column packed with the sulfuric acid silica gel layer stacked on the silver nitrate silica gel layer and a second column packed with the alumina layer and attachable to and detachable from the silver nitrate silica gel layer side of the first column, for example.

In this extraction method, the direction in which the hydrophobic solvent is supplied to the alumina layer can be set arbitrarily. That is, the direction in which the hydrophobic solvent is supplied to the alumina layer may be set at the same or opposite direction in which the aliphatic hydrocarbon solvent is passed. However, when the columns used are the first and second columns wherein the second column is packed with the alumina layer as described above, the hydrophobic solvent is supplied to and passed through the alumina layer, preferably in a direction opposite to the direction in which the aliphatic hydrocarbon solvent is passed. In the alumina layer, polychlorinated biphenyls are captured mainly at the end on the supply side of the aliphatic hydrocarbon solvent. Accordingly, when a hydrophobic solvent is supplied to the alumina layer in a direction opposite to the direction in which the aliphatic hydrocarbon solvent is passed, polychlorinated biphenyls captured by the alumina layer are rapidly extracted from the alumina layer with a small amount of the hydrophobic solvent. Accordingly, the amount of the solution of polychlorinated biphenyls in the hydrophobic solvent, obtained by this extraction method, can be made so small that the solution can be easily applied to decomposition treatment (detoxifying treatment) of polychlorinated biphenyls and to various analyses.

Preferably, the extraction method of the present invention further includes a step of allowing the aliphatic hydrocarbon solvent passed through the sulfuric acid silica gel layer to be supplied to, and passed through, a metal salt hydrate silica gel layer before the aliphatic hydrocarbon solvent is supplied to the silver nitrate silica gel layer. According to this extraction method using the metal salt hydrate silica gel layer, the extraction rate (recovery rate) of polychlorinated biphenyls having a small number of chlorine atoms can be increased, and thus the extraction rate (recovery rate) of polychlorinated biphenyls contained in the oily liquid can be further increased.

The metal salt hydrate silica gel layer used herein is preferably a copper salt hydrate silica gel layer, for example.

In the extraction method of the present invention, the aliphatic hydrocarbon solvent may be supplied to and passed through a carbon material layer in the process until the aliphatic hydrocarbon solvent passed through the sulfuric acid silica gel layer is supplied to the alumina layer. The carbon material layer is preferably a layer made of graphite.

In the extraction method using the carbon material layer, impurity substances, particularly polychlorinated naphthalenes, contained in an oily liquid can be captured and removed by the carbon material layer, so that polychlorinated biphenyls can be extracted with high purity from the oily liquid. Accordingly, the extraction method using the carbon material layer is particularly effective when polychlorinated biphenyls are extracted from an oily liquid further containing polychlorinated naphthalenes, for example an electric insulating oil consisting of mineral oils.

In the extraction method of the present invention, a hydrocarbon solvent having a boiling point not lower than the heating temperature of the sulfuric acid silica gel layer and being capable of dissolving an oily liquid can, together with the oily liquid, be added to the sulfuric acid silica gel layer. By this addition, the oily liquid is diluted with the hydrocarbon solvent, so that the efficiency of contact between the oily liquid and the sulfuric acid silica gel layer can be improved to increase the reaction efficiency. In the sulfuric acid silica gel layer, therefore, impurity components, particularly aromatic compounds, other than polychlorinated biphenyls contained in the oily liquid can be decomposed in a shorter time, and the time required for extraction of polychlorinated biphenyls can be reduced.

Preferably, the extraction method of the present invention usually further includes a step of removing the aliphatic hydrocarbon solvent remaining in the alumina layer, before the hydrophobic solvent is supplied to the alumina layer. By this removal, an extract of higher purity with less contamination with the aliphatic hydrocarbon solvent and impurity components dissolved therein, that is, a solution of polychlorinated biphenyls in the hydrophobic solvent can be obtained, and the volume of the solution in the hydrophobic solvent can be further reduced.

In the extraction method of the present invention, it is usually preferable that the alumina layer is supplied with a hydrophobic solvent while the alumina layer is heated to at least 35° C. By so doing, polychlorinated biphenyls captured by the alumina layer can be extracted with a smaller amount of the hydrophobic solvent, and thus the volume of the resulting solution of polychlorinated biphenyls in the hydrophobic solvent can be further reduced.

Another aspect of the present invention relates to a method for measuring polychlorinated biphenyls contained in a polychlorinated biphenyls-containing oily liquid. This measurement method includes the steps of: adding a sample collected from an oily liquid to a sulfuric acid silica gel layer, allowing the sulfuric acid silica gel layer to which the sample is added to be kept in a state heated to at least 35° C. for a predetermined time and then cooling the layer to ordinary temperature, supplying an aliphatic hydrocarbon solvent to the sulfuric acid silica gel layer cooled to ordinary temperature, allowing the aliphatic hydrocarbon solvent passed through the sulfuric acid silica gel layer to be supplied to, and passed through, a silver nitrate silica gel layer, allowing the aliphatic hydrocarbon solvent passed through the silver nitrate silica gel layer to be supplied to, and passed through, an alumina layer, allowing a hydrophobic solvent capable of dissolving polychlorinated biphenyls to be supplied to, and passed through, the alumina layer, securing the hydrophobic solvent passed through the alumina layer, and analyzing the secured hydrophobic solvent by gas chromatography.

In this measurement method, when the sulfuric acid silica gel layer to which a sample collected from an oily liquid is added is kept in a state heated to at least 35° C. for a predetermined time, impurity components (particularly aromatic compounds when the oily liquid is an electric insulating oil consisting of mineral oils) other than polychlorinated biphenyls contained in the sample are rapidly decomposed by reaction with the sulfuric acid silica gel layer. The resultant decomposition products, together with polychlorinated biphenyls, are retained in the sulfuric acid silica gel layer. Then, when the sulfuric acid silica gel layer cooled to ordinary temperature is supplied with an aliphatic hydrocarbon solvent, the aliphatic hydrocarbon solvent is passed through the sulfuric acid silica gel layer and supplied to the silver nitrate silica gel layer, and then passed through the silver nitrate silica gel layer. On this occasion, the polychlorinated biphenyls and a part of the decomposition products retained in the sulfuric acid silica gel layer are dissolved in the aliphatic hydrocarbon solvent supplied to the sulfuric acid silica gel layer and are supplied from the sulfuric acid silica gel layer to the silver nitrate silica gel layer. Then, a part of the decomposition products contained in the aliphatic hydrocarbon solvent supplied to the silver nitrate silica gel layer is adsorbed by, and retained in, the silver nitrate silica gel layer. The polychlorinated biphenyls contained in the aliphatic hydrocarbon solvent supplied to the silver nitrate silica gel layer remain dissolved in the aliphatic hydrocarbon solvent and are passed through the silver nitrate silica gel layer.

Next, when the aliphatic hydrocarbon solvent passed through the silver nitrate silica gel layer, that is, the aliphatic hydrocarbon solvent in which the polychlorinated biphenyls are dissolved, is supplied to and passed through the alumina layer, the polychlorinated biphenyls dissolved in the aliphatic hydrocarbon solvent are captured by the alumina layer, while impurity components (mainly paraffins when the oily liquid is an electric insulating oil consisting of mineral oils) other than polychlorinated biphenyls, remaining in the aliphatic hydrocarbon solvent, are not captured by the alumina layer but passed together with the aliphatic hydrocarbon solvent through the alumina layer. Then, when a hydrophobic solvent is supplied to and passed through the alumina layer through which the aliphatic hydrocarbon solvent was passed, the polychlorinated biphenyls captured by the alumina layer are dissolved in the hydrophobic solvent, eluted from the alumina layer and secured as a solution in the hydrophobic solvent. The thus obtained solution of polychlorinated biphenyls in the hydrophobic solvent can be applied to analysis by gas chromatography directly or after being suitably concentrated.

As described above, an analytical sample of polychlorinated biphenyls can be prepared from a polychlorinated biphenyls-containing oily liquid sample in a short time by an easy operation in the measurement method of the present invention, so that polychlorinated biphenyls in the oily liquid can be measured rapidly by gas chromatography.

In this measurement method, the sulfuric acid silica gel layer, the silver nitrate silica gel layer and the alumina layer are usually packed in a column. For example, the sulfuric acid silica gel layer and the silver nitrate silica gel layer are stacked and packed in a first column, and the alumina layer is packed in a second column attachable to and detachable from the silver nitrate silica gel layer side of the first column.

In this measurement method, a hydrophobic solvent is supplied to and passed through the alumina layer, usually in a direction opposite to the direction in which the aliphatic hydrocarbon solvent is passed through the alumina layer. In the alumina layer, polychlorinated biphenyls are captured mainly at the end on the supply side of the aliphatic hydrocarbon solvent. Accordingly, when a hydrophobic solvent is supplied to the alumina layer in a direction opposite to the direction in which the aliphatic hydrocarbon solvent is passed, polychlorinated biphenyls captured by the alumina layer are rapidly extracted from the alumina layer with a small amount of the hydrophobic solvent. As a result, the solution of polychlorinated biphenyls in the hydrophobic solvent, obtained by this measurement method, serves as an analytical sample in a small volume suitable for analysis by gas chromatography, and thus the sample can be easily applied to analysis by gas chromatography directly or after being slightly concentrated.

This measurement method can be modified in the same manner as in the extraction method described above. That is, the measurement method may further include a step of allowing the aliphatic hydrocarbon solvent passed through the sulfuric acid silica gel layer to be supplied to, and passed through, a metal salt hydrate silica gel layer, for example a copper salt hydrate silica gel layer, before the aliphatic hydrocarbon solvent is supplied to the silver nitrate silica gel layer. Further, the aliphatic hydrocarbon solvent may be supplied to and passed through a carbon material layer, for example a layer made of graphite, in the process until the aliphatic hydrocarbon solvent passed through the sulfuric acid silica gel layer is supplied to the alumina layer. The measurement method using such a carbon material layer is particularly effective in measuring polychlorinated biphenyls contained in an oily liquid further containing polychlorinated naphthalenes, for example an electric insulating oil consisting of mineral oils. In this measurement method, a hydrocarbon solvent having a boiling point not lower than the heating temperature of the sulfuric acid silica gel layer and being capable of dissolving an oily liquid can, together with the oily liquid, be added to the sulfuric acid silica gel layer. Further, the measurement method may further include a step of removing the aliphatic hydrocarbon solvent remaining in the alumina layer, before the hydrophobic solvent is supplied to the alumina layer. In this measurement method, the alumina layer is supplied with the hydrophobic solvent, while the alumina layer is heated to at least 35° C.

The gas chromatographic method used in the measurement method of the present invention is a method suitable for measurement of a trace amount of polychlorinated biphenyls and is usually one method selected from gas chromatography-mass spectrometry and gas chromatography-electron capture detection.

Still another aspect of the present invention relates to a column used for extracting polychlorinated biphenyls from a polychlorinated biphenyls-containing oily liquid. This column includes a first column packed from one end to the other end with a sulfuric acid silica gel layer, a metal salt hydrate silica gel layer and a silver nitrate silica gel layer in this order and a second column packed with an alumina layer and attachable to and detachable from the other end of the first column.

In these columns, the first column is preferably further packed with a carbon material layer in an arbitrary position from the sulfuric acid silica gel layer to the other end. Particularly, this carbon material layer is packed preferably between the sulfuric acid silica gel layer and the metal hydrate silica gel layer.

The column in another aspect of the invention is used similarly for extracting polychlorinated biphenyls from a polychlorinated biphenyls-containing oily liquid, and includes a first column packed with a sulfuric acid silica gel layer, a metal salt hydrate silica gel layer and a silver nitrate silica gel layer in this order, a second column packed with an alumina layer, and a third column packed with a carbon material layer. The third column connects the end, at the side of the silver nitrate silica gel layer, of the first column detachably to one end of the second column.

When the respective columns for extraction of polychlorinated biphenyls as described above are used for carrying out the extraction or measurement method of the present invention, the extraction rate (recovery rate) of polychlorinated biphenyls can be increased, and the measurement accuracy of polychlorinated biphenyls can be improved.

The column in still another aspect of the invention is used in purifying an oily liquid in a process of extracting polychlorinated biphenyls from a polychlorinated biphenyls-containing oily liquid, and is packed from one end to the other end with a sulfuric acid silica gel layer, a metal salt hydrate silica gel layer and a silver nitrate silica gel layer in this order. This column is further packed preferably with a carbon material layer in an arbitrary position from the sulfuric acid silica gel layer to the other end. Particularly, this carbon material layer is packed preferably between the sulfuric acid silica gel layer and the metal salt hydrate silica gel layer.

When such a column for purification of a polychlorinated biphenyls-containing oily liquid is used for carrying out the extraction or measurement method of the present invention, the extraction rate (recovery rate) of polychlorinated biphenyls can be increased, and the measurement accuracy of polychlorinated biphenyls can be improved.

Still another aspect of the invention relates to a treating agent for purifying a polychlorinated biphenyls-containing oily liquid in a process of extracting polychlorinated biphenyls from the oily liquid, and this treating agent is made of metal salt hydrate silica gel. When this treating agent is used in the extraction method, the measurement method or the column of the present invention, the extraction rate (recovery rate) of polychlorinated biphenyls having a small number of chlorine atoms can be increased, and thus the extraction rate (recovery rate) of the whole of polychlorinated biphenyls from an oily liquid can be increased, and the measurement accuracy of polychlorinated biphenyls contained in the oily liquid can be improved.

Other objects and effects of the present invention will be described in the following detailed description.

BEST MODE FOR CARRYING OUT THE INVENTION

The method for extracting polychlorinated biphenyls (PCBs) according to the present invention relates to a method for extracting PCBs from an oily liquid containing PCBs. The oily liquid containing PCBs includes, for example, electric insulating oils used in electric instruments such as transformers and capacitors, waste organic solvents containing PCBs formed in chemical experiments and chemical factories, extracts obtained for analysis by extracting PCBs with an organic solvent, from PCBs-containing samples, and decomposition treatment liquids and washes generated in facilities for decomposition treatment of PCBs. The electric insulating oils are composed of mineral oils consisting primarily of paraffin having relatively high-boiling point, naphthene or aromatic compounds obtained usually by rectifying petroleum, and may contain PCBs when PCBs are added for the purpose of increasing electrical insulating properties or when PCBs are mixed during a production process.

PCBs are those containing homologs having 1 to 10 chlorine atoms. However, PCBs contained in the electric insulating oils mentioned above are usually those having 2 to 8 chlorine atoms.

Figure 1:
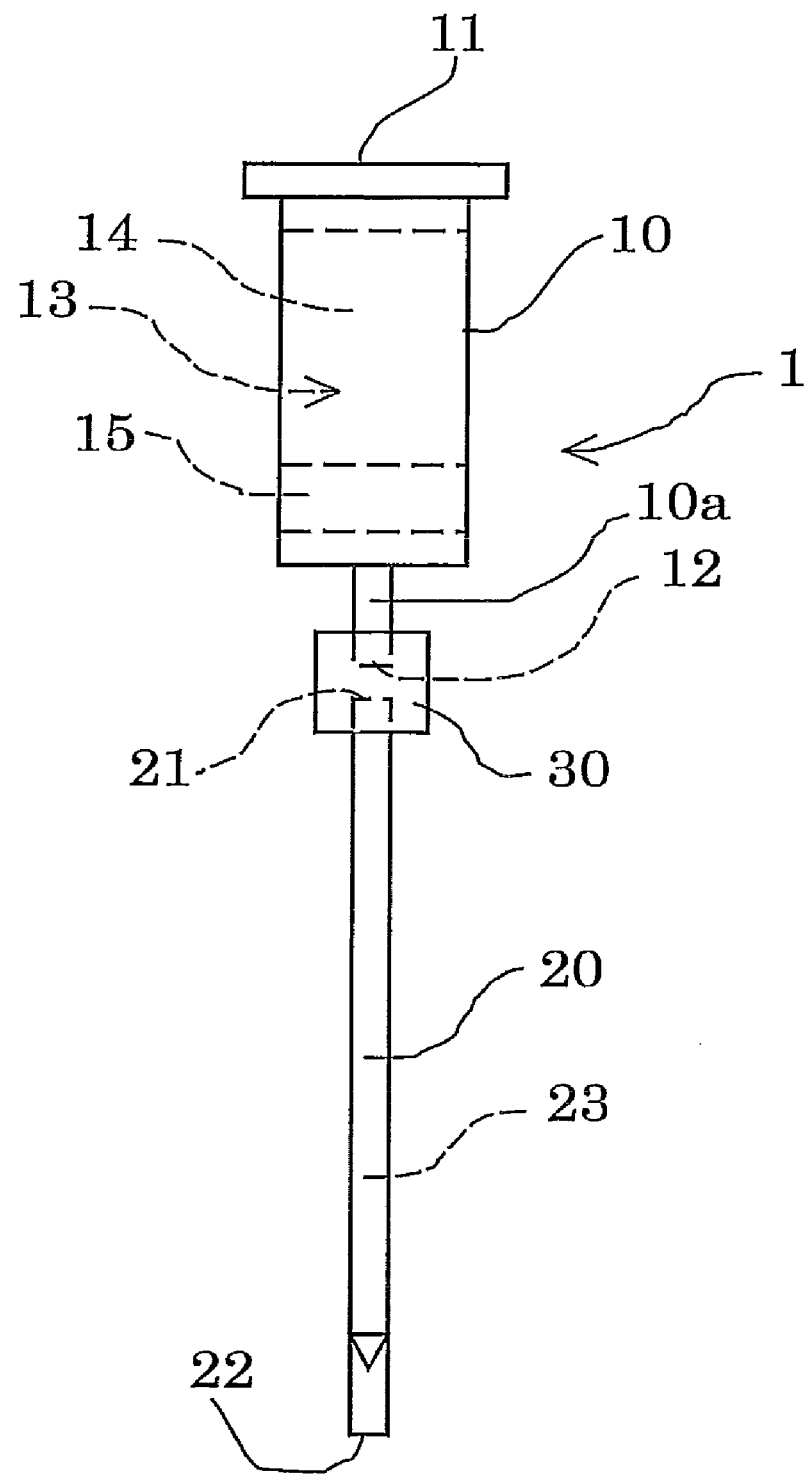
FIG. 1 is a schematic diagram of one example of the column utilizable in the method for extracting PCBs in the present invention.

One example of the column used for carrying out the method for extracting PCBs in the present invention will be described with reference to FIG. 1. In this diagram, a column 1 is provided mainly with a first column 10, a second column 20, and a connecting member 30 for connecting the columns 10 and 20 to each other.

The first column 10 is formed in a cylindrical shape with the lower end 10a having reduced outer and inner diameters, and has openings 11 and 12 at the upper and lower ends, respectively. The first column 10 is formed for example of glass or solvent- and heat-resistant plastic, which is packed inside with multilayer silica gel 13. The multilayer silica gel 13 consists of an upper layer 14 stacked on a lower layer 15.

The upper layer 14 is a layer filled with sulfuric acid silica gel, that is, a sulfuric acid silica gel layer, and the sulfuric acid silica gel used herein is prepared by adding concentrated sulfuric acid uniformly to the surface of silica gel. The bulk density of sulfuric acid silica gel in the upper layer 14 is not particularly limited, and is usually preferably set at 0.3 to 1.1 $g/cm^3$, more preferably 0.5 to 1.0 $g/cm^3$.

The lower layer 15, on the other hand, is a layer filled with silver nitrate silica gel, that is, a silver nitrate silica gel layer, and the silver nitrate silica gel used herein is prepared by adding an aqueous solution of silver nitrate uniformly to the surface of silica gel and then removing water by heating under reduced pressure. The bulk density of silver nitrate silica gel in the lower layer 15 is not particularly limited, and is usually preferably set at 0.3 to 0.8 $g/cm^3$, more preferably 0.4 to 0.7 $g/cm^3$.

Because silver nitrate does not have hydration water, the silver nitrate silica gel prepared by using an aqueous solution thereof is different from metal salt hydrate silica gel described later.

In the multilayer silica gel 13, the ratio of the upper layer 14 to the lower layer 15 is established such that the weight ratio of the sulfuric acid silica gel to the silver nitrate silica gel is preferably 1.0 to 50, more preferably 3.0 to 30. When the weight ratio of the sulfuric acid silica gel is higher than 50, the ratio of the silver nitrate silica gel is reduced, so purification of an electric insulating oil by adsorption action may become insufficient. On the other hand, when the weight ratio of the sulfuric acid silica gel is lower than 1.0, purification of an electric insulating oil by decomposition action may become insufficient.

The second column 20 is formed in a cylindrical shape with outer and inner diameters set appropriately identical with those of the lower end 10a of the first column 10, and has openings 21 and 22 at the upper and lower ends, respectively. The second column 20 is formed for example of glass or solvent- and heat-resistant plastic, which is packed inside with a layer filled with alumina, that is, an alumina layer 23.

The alumina used in the alumina layer 23 is not particularly limited as long as it is capable of adsorbing PCBs, and may be any one of basic alumina, neutral alumina and acidic alumina. The alumina may be one having various degrees of activity.

The bulk density of alumina in the alumina layer 23 is not particularly limited, and is usually preferably set at 0.5 to 1.2 $g/cm^3$, more preferably 0.8 to 1.1 $g/cm^3$.

The connecting member 30, which is a cylindrical member into which the lower end 10a of the first column 10 and the upper end of the second column 20 can be inserted, is formed of a material (for example solvent- and heat-resistant plastic) stable to various solvents, particularly hydrocarbon solvents.

With the connecting member 30, the lower end 10a of the first column 10 and the upper end of the second column 20 are detachably connected to each other. It follows that in the column 1 consisting of the first column 10 and the second column 20, the portion of the alumina layer 23 can be separated independently from the upper layer 14 and the lower layer 15.

The size of the column 1 can be set appropriately depending on the purpose of extraction of PCBs from an oily liquid described later. For example, when the extraction of PCBs from an oily liquid is intended in pretreatment of the oily liquid to measure the concentration of PCBs contained therein, it is only necessary that a small or trace amount of a sample be collected from the oily liquid and subjected to the extraction method of the present invention, and as a consequence, the column 1 can be set small-sized. On the other hand, when the extraction of PCBs from an oily liquid is intended in decomposition treatment (detoxifying treatment) of PCBs extracted from the oily liquid, it is necessary that a relatively large amount of the oily liquid be treated, and thus the column 1 can be set large-sized depending on the amount of the oily liquid to be treated.

For example, when PCBs are to be extracted from about 1.0 to 500 mg of a sample collected from an oily liquid in order to measure the concentration of PCBs contained in the oily liquid, the size of the first column 10 (the size of that portion of the column which can be packed with the upper layer 14 and the lower layer 15) in the column 1 is preferably 10 to 20 mm in inner diameter and 30 to 110 mm in length, and the size of the second column 20 (the size of that portion of the column which can be packed with the alumina layer 23) is preferably 2.0 to 10.0 mm in inner diameter and 10 to 200 mm in length.

Hereinafter, the method for extracting PCBs with the said column 1 will be described, in which PCBs are extracted from an oily liquid, mainly for the purpose of measuring the concentration of PCBs contained in the oily liquid.

Figure 2:
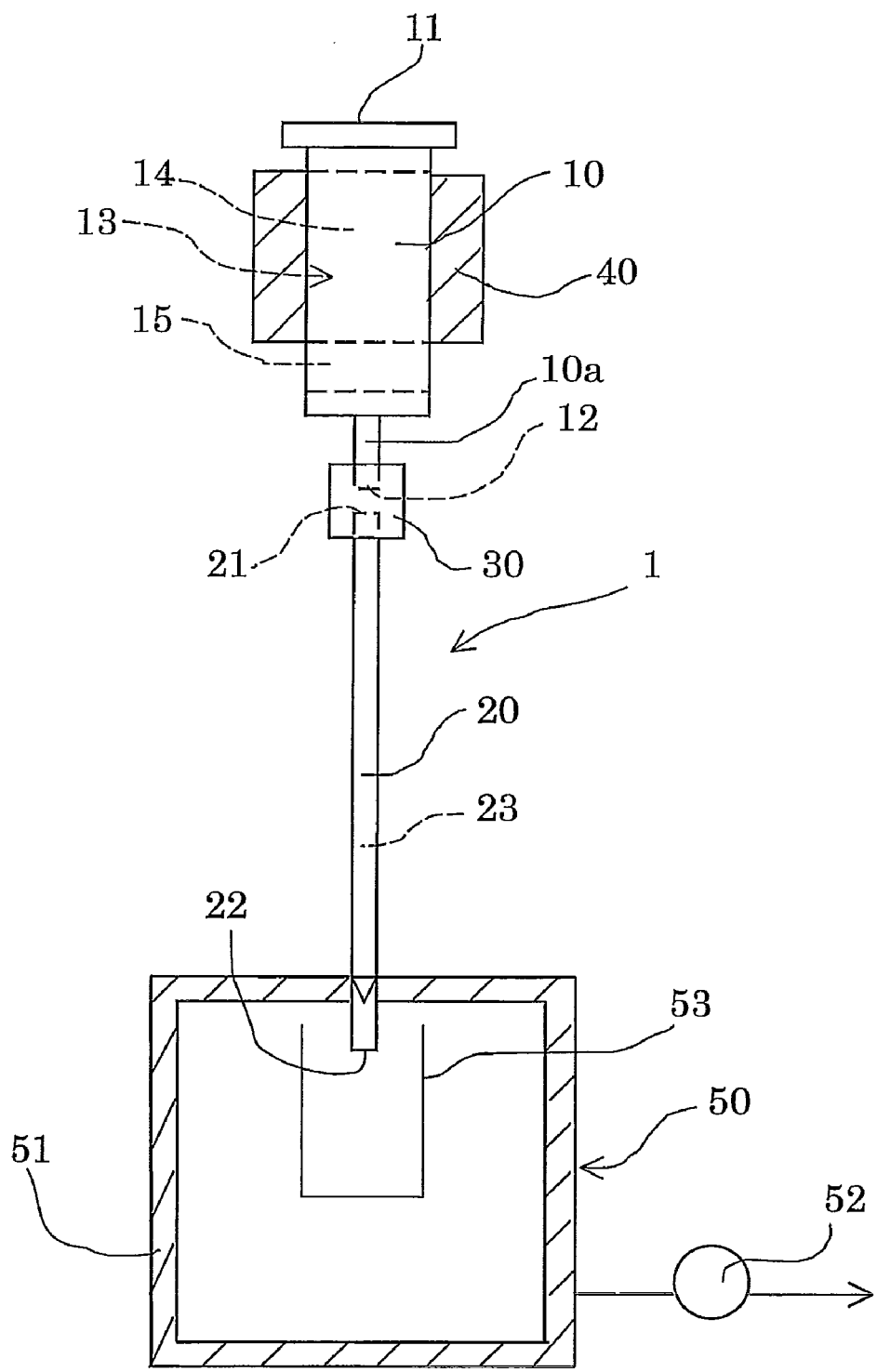
FIG. 2 is a diagram showing one step of the extraction operation using the above column.

In this extraction method, first, a first heating unit 40 is arranged around the upper layer 14 of the first column 10, and a suction unit 50 is arranged in the lower end of the second column 20, as shown in FIG. 2. The first heating unit 40 is a heater, a Peltier device or the like and is used to heat the whole of the upper layer 14 to a necessary temperature. The suction unit 50 includes a container 51 capable of hermetically accommodating the lower end of the second column 20 and a pump 52 for depressurizing the container 51. The container 51 is provided therein with a solvent container 53 for receiving an aliphatic hydrocarbon solvent described later after passage through the column 1.

Next, a small or trace amount (usually about 1.0 to 500 mg) of a sample is collected from an oily liquid, and this sample is introduced through the opening 11 of the upper end of the first column 10 into the upper layer 14. Then, the first heating unit 40 is activated thereby heating the upper layer 14 and keeping it heated for a predetermined time. The added sample is retained in the upper layer 14 in the first column 10. By so doing, impurities (particularly aromatic compounds) other than PCBs contained in the sample are rapidly decomposed by reacting with the sulfuric acid silica gel in the upper layer 14. Decomposition products from this reaction are captured by the upper layer 14 and retained in the first column 10.

In this process, the heating temperature of the upper layer 14 is set at 35° C. or more, preferably 50° C. or more, more preferably 60° C. or more. The upper limit of the heating temperature is not particularly limited, and is usually about 90° C. When the heating temperature is lower than 35° C., the reaction between the impurities contained in the sample and the sulfuric acid silica gel becomes hardly advanced, thus making it difficult to extract PCBs in a short time from the sample. Usually, the heating time of the upper layer 14 is set preferably at a period of from 10 minutes to 8 hours. When the heating time is less than 10 minutes, decomposition of the impurities contained in the sample becomes insufficient so that the finally obtained extract may be contaminated with impurity components other than PCBs.

When the oily liquid contains or may contain a large amount of impurity components other than PCBs, it is preferable in this process that while the sample is added to the upper layer 14 in the first column 10, a hydrocarbon solvent capable of dissolving the sample (that is, the oily liquid) is added to the upper layer 14. By so doing, the sample is diluted with the hydrocarbon solvent, thereby improving the efficiency of contact of the sample with the sulfuric acid silica gel to increase the reaction efficiency. Accordingly, impurity components (particularly aromatic compounds) other than PCBs contained in the sample are efficiently decomposed in a shorter time in the upper layer 14, and as a consequence, the time required for extraction of PCBs can be reduced.

The hydrocarbon solvent that can be used herein is usually a C5 to C8 aliphatic saturated hydrocarbon solvent, for example n-pentane, n-hexane, n-heptane, n-octane, isooctane or cyclohexane. However, it is necessary to select a hydrocarbon solvent having a boiling point not lower than the heating temperature of the upper layer 14. When the boiling point of the hydrocarbon solvent does not satisfy this condition, the hydrocarbon solvent will rapidly volatilize during heating of the first column 10, and thus the reaction efficiency is hardly increased.

Usually, the hydrocarbon solvent may be added continuously after addition of the sample, to the upper layer 14 in the first column 10, or may be previously added to the sample.

The upper layer 14 heated for a predetermined time in the process described above is then cooled to ordinary temperatures (usually room temperature at about 10 to 30° C.) by detaching the first heating unit 40 or by turning off a switch of the first heating unit 40 and leaving the layer as it is.

Figure 3:
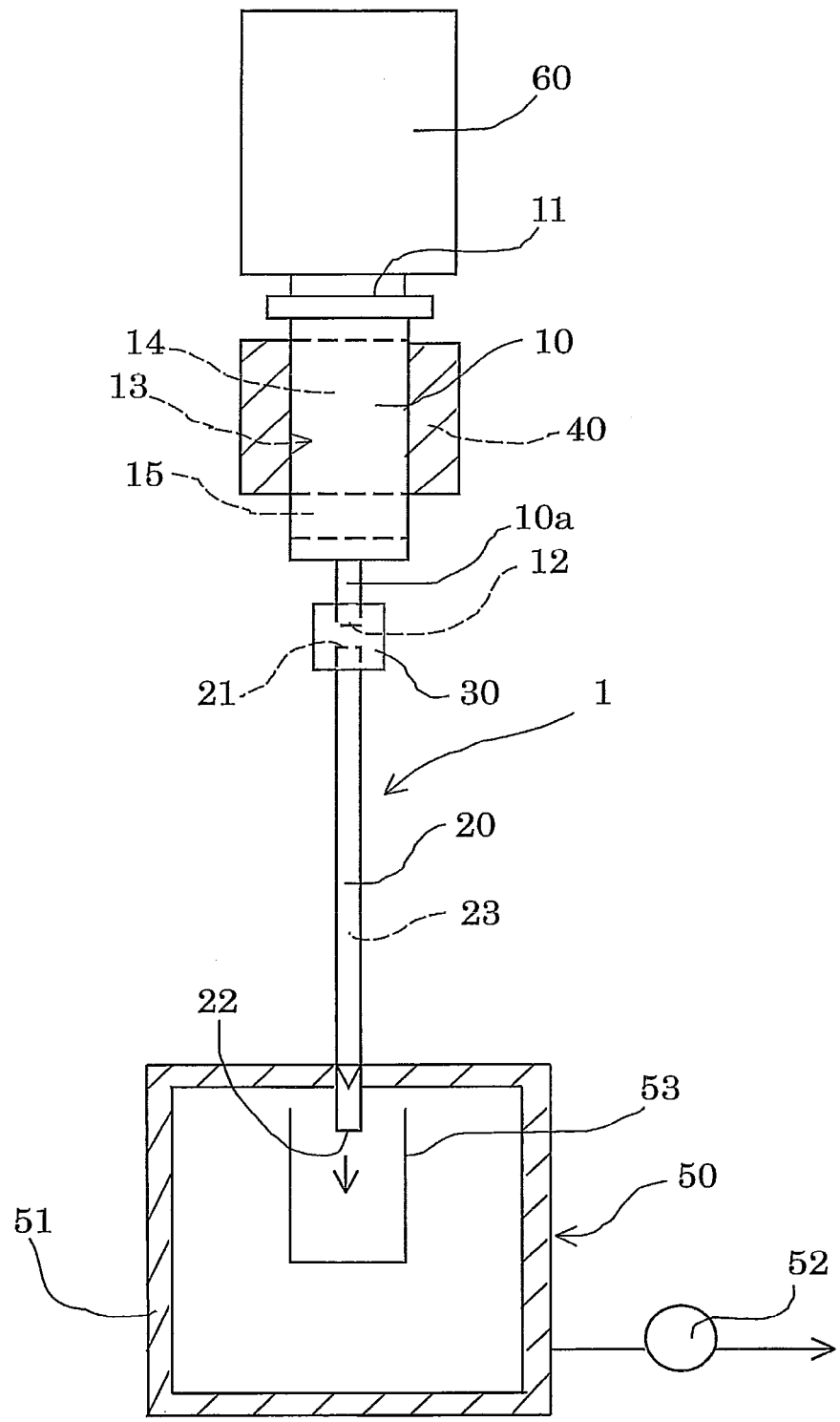
FIG. 3 is a diagram showing another step of the extraction operation using the above column.

As shown in FIG. 3, a first reservoir 60 for supplying a solvent to the first column 10 is then fitted into the opening 11, at the side of the upper end, of the first column 10, and an aliphatic hydrocarbon solvent is stored in the first reservoir 60. When the pump 52 is actuated, the container 51 is depressurized so that the aliphatic hydrocarbon solvent stored in the first reservoir 60 is supplied continuously and gradually to the first column 10. The aliphatic hydrocarbon solvent supplied from the first reservoir 60 to the first column 10 is supplied to the upper layer 14, then passed through the upper layer 14, supplied to the lower layer 15, and passed through the lower layer 15. Then, the aliphatic hydrocarbon solvent passed through the lower layer 15 is passed from the opening 12 of the first column 10 via the connecting member 30 and flowed from the opening 21 into the second column 20. On this occasion, PCBs retained in the upper layer 14 are dissolved in the aliphatic hydrocarbon solvent and passed, together with the aliphatic hydrocarbon solvent, through the lower layer 15 and flowed into the second column 20. On the other hand, a part of decomposition products retained in the upper layer 14 is dissolved in the aliphatic hydrocarbon solvent, transferred to the lower layer 15, adsorbed into the silver nitrate silica gel, and retained in the first column 10.

The aliphatic hydrocarbon solvent flowed into the second column 20 is supplied to the alumina layer 23 in the second column 20, passed through this layer, discharged from the opening 22 and received by the solvent container 53 in the container 51. On this occasion, PCBs dissolved in the aliphatic hydrocarbon solvent from the first column 10 are captured by the alumina layer 23 and retained in the second column 20. Particularly, PCBs are easily captured by the alumina layer 23 and thus retained mainly in the vicinity of the opening 21 in the upper end of the second column 20. On the other hand, paraffins that are impurity components other than aromatic compounds contained in the sample are dissolved in the aliphatic hydrocarbon solvent from the first reservoir 60, then passed, together with the aliphatic hydrocarbon solvent, through the alumina layer 23, and received by the solvent container 53.

The aliphatic hydrocarbon solvent used in this process is capable of dissolving PCBs retained in the first column 10 and is usually a C5 to C8 aliphatic saturated hydrocarbon solvent, for example n-pentane, n-hexane, n-heptane, n-octane, isooctane or cyclohexane. Particularly, n-hexane is preferable. Usually, the amount of the aliphatic hydrocarbon solvent stored in the first reservoir 60, that is, the total amount of the aliphatic hydrocarbon solvent supplied to the first column 10, is preferably set at 10 to 120 mL. Usually, the rate of feed of the aliphatic hydrocarbon solvent from the first reservoir 60 is preferably set at 0.2 to 5.0 mL/min. by regulating the depressurized state of the container 51 with the pump 52.

Figure 4:
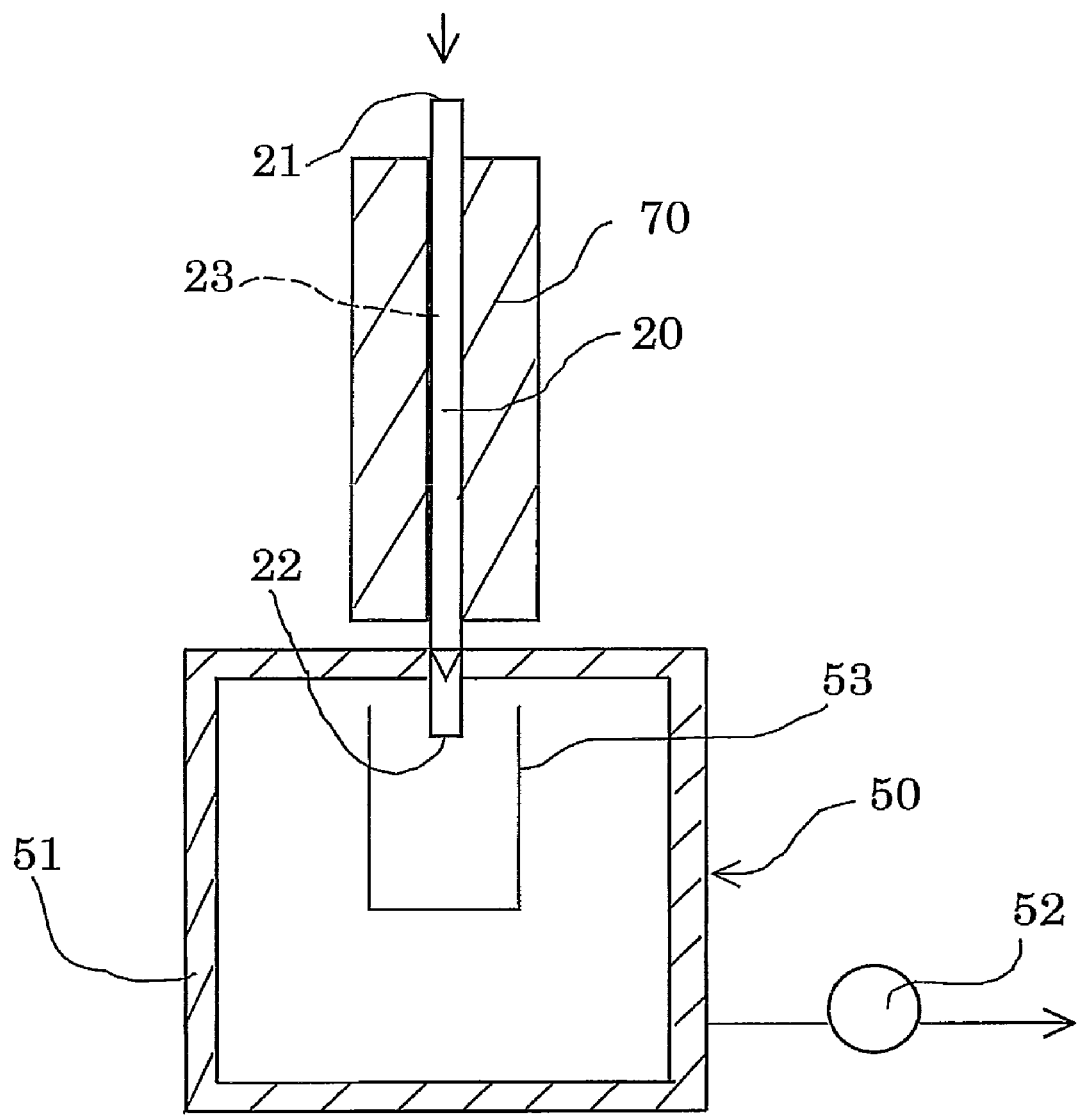
FIG. 4 is a diagram showing still another step of the extraction operation using the above column.

Next, the connecting member 30 is detached to separate the second column 20 from the first column 10, and as shown in FIG. 4, a second heating unit 70 is arranged around the second column 20. The second heating unit 70 used herein is one similar to the first heating unit 40. Then, while the second column 20 is heated to about 35 to 90° C. with the second heating unit 70, the pump 52 is actuated thereby supplying the second column 20 via the upper-end opening 21 with an inert gas such as nitrogen gas or with air. By so doing, the solvent such as the aliphatic hydrocarbon solvent remaining in the second column 20, together with the inert gas, is discharged from the opening 22 at the lower end of the second column 20, thereby removing the solvent such as the aliphatic hydrocarbon solvent from the alumina layer 23. As a result, the alumina layer 23 in the second column 20 is dry-treated.

Figure 5:
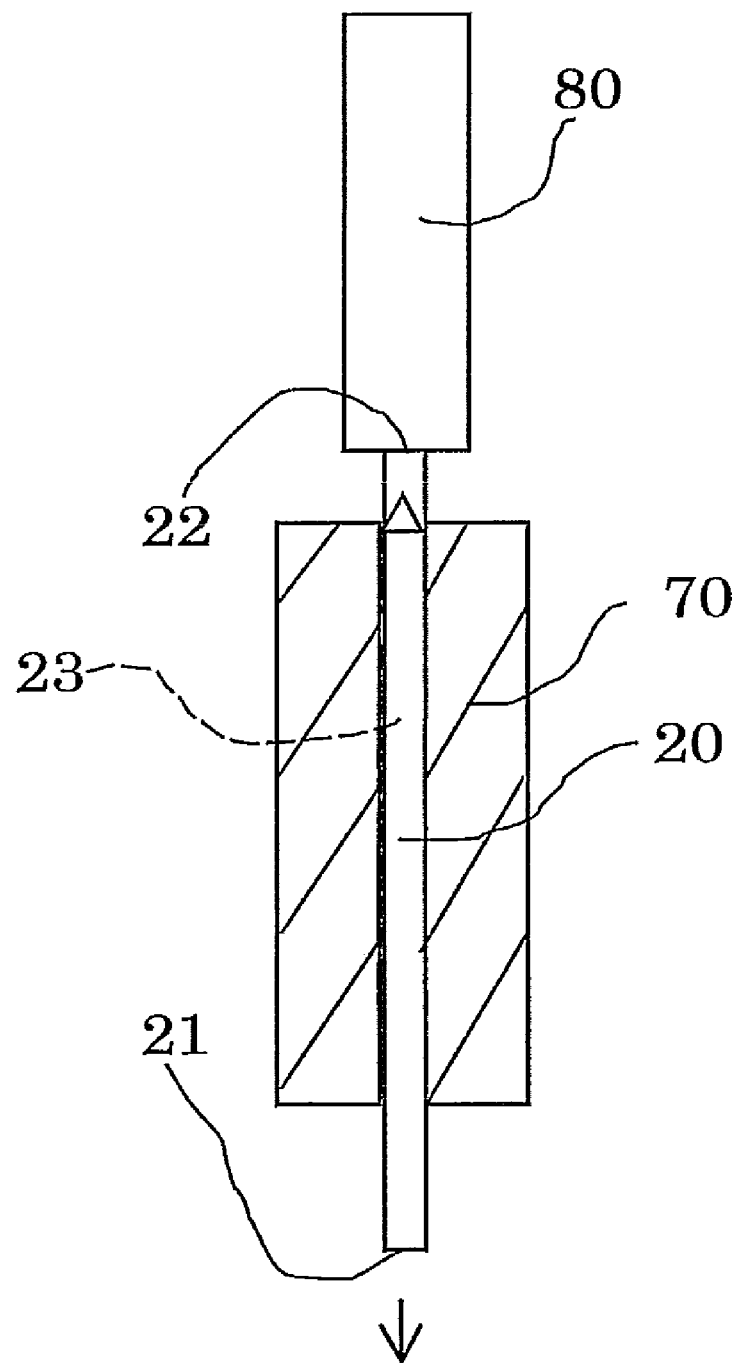
FIG. 5 is a diagram showing still another step of the extraction operation using the above column.

Then, the second column 20 is detached from the suction unit 50 and then turned upside down by inverting it together with the second heating unit 70. As shown in FIG. 5, the opening 22 of the second column 20 thus turned up by inversion is then provided with a second reservoir 80 for supplying a solvent into the opening 22, and the second reservoir 80 is supplied with a predetermined amount of a hydrophobic solvent.

The hydrophobic solvent supplied to the second reservoir 80 flows naturally by its own weight from the second reservoir 80 into the second column 20, and is thereby supplied to the alumina layer 23, passed through the alumina layer 23, and discharged from the opening 21 of the second column 20 that was directed downward by inversion. On this occasion, the hydrophobic solvent from the second reservoir 80 dissolves PCBs captured by the alumina layer 23, and together with the PCBs, is discharged from the opening 21. Accordingly, when the hydrophobic solvent discharged from the opening 21 is secured, a solution of PCBs in the hydrophobic solvent, that is, the objective extract of PCBs can be obtained. PCBs have been captured mainly in the vicinity of the opening 21 side of the alumina layer 23, so that substantially the total amount of PCBs that are captured by the alumina layer 23 comes to be dissolved in the hydrophobic solvent mainly in a first eluate discharged from the second column 20. Accordingly, the objective extract of PCBs can be obtained by merely securing the hydrophobic solvent in a first eluate discharged from the opening 21. This extract consists of the first eluate of low volume as described above and is thus in such a small volume as to be easily utilizable in the analytical operation described later. In addition, the extract of PCBs obtained herein is one obtained by previously removing the aliphatic hydrocarbon solvent from the alumina layer 23 and then supplying the hydrophobic solvent to the second column 20, so that the extract is highly pure with less contamination with the aliphatic hydrocarbon solvent and impurity components dissolved therein.

According to the extraction method in this embodiment, the above-described extract can be obtained usually in a short time of about 2 to 10 hours from the step of initiating the operation (the step of adding a sample to the first column 10).

In such an extraction step, the second column 20 is supplied with a hydrophobic solvent preferably under heating with the second heating unit 70. The heating temperature of the second column 20 is usually set such that the temperature of the alumina layer 23 reaches preferably 35° C. or more, more preferably 60° C. or more. The upper limit of the heating temperature is not particularly limited and is usually about 90° C. When the second column 20 is thus heated, the whole amount of PCBs captured by the alumina layer 23 becomes easily extractable with a smaller amount of the hydrophobic solvent, and thus the amount of the extract of PCBs can be set smaller to be further utilizable in the analytical operation described later.

The hydrophobic solvent used in this extraction step is not particularly limited as long as it is capable of dissolving PCBs. Usually, the hydrophobic solvent is toluene, a mixed solvent of toluene and an aliphatic hydrocarbon solvent (for example, n-pentane, n-hexane, n-heptane, n-octane, isooctane or cyclohexane), or a mixed solvent of an organochlorine solvent (for example, dichloromethane, trichloromethane or tetrachloromethane) and an aliphatic hydrocarbon solvent (for example, n-pentane, n-hexane, n-heptane, n-octane, isooctane or cyclohexane). Among them, toluene is preferable because by using it in a smaller amount, PCBs can be extracted from the alumina layer 23.

When the concentration of PCBs contained in the oily liquid is determined, the extract obtained in the extraction operation, that is, the solution of PCBs in the hydrophobic solvent, is used as a sample for analysis by gas chromatography. Gas chromatography can be carried out with gas chromatographic units equipped with various detectors. Usually, gas chromatography-mass spectrometry (GC-MS method) or gas chromatography-electron capture detection (GC/ECD method), which is highly sensitive to PCBs, is preferably used. Particularly when the GC/MS method is used, PCBs contained in a sample for analysis can be quantified in units of isomers and homologs, and thus many findings can be obtained from analysis results.

The extract obtained by the extraction operation described above may be used after being concentrated as necessary for analysis by gas chromatography.

Figure 6:
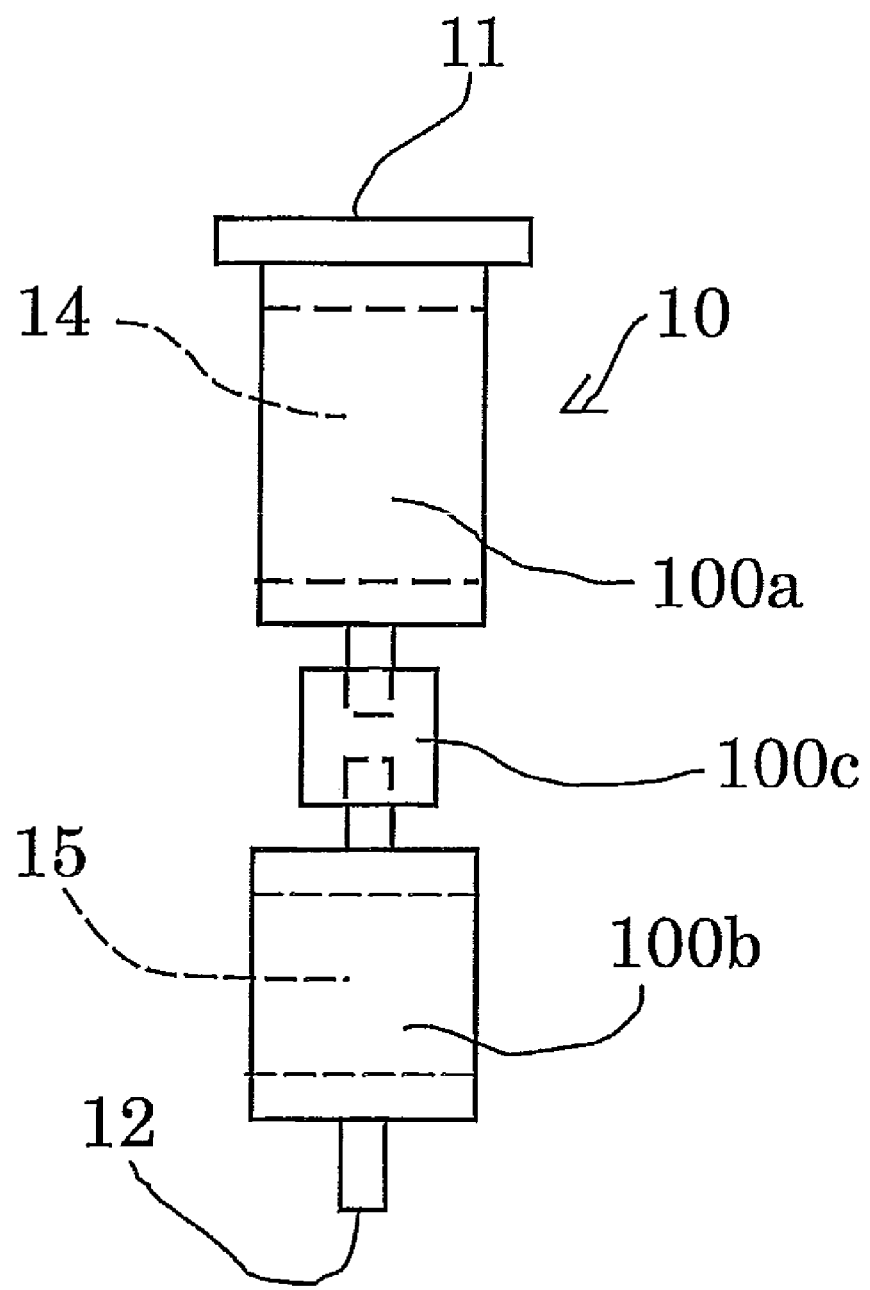
FIG. 6 is a partial schematic diagram of another example of the column utilizable in the method for extracting PCBs in the present invention.

The embodiment described above can be modified for example as follows:

(1) In the column 1 in the embodiment described above, the first column 10 is composed of a single column packed with the multilayer silica gel 13 in which the upper layer 14 made of sulfuric acid silica gel and the lower layer 15 made of silver nitrate silica gel are stacked. Alternatively, as shown in FIG. 6, the first column 10 may be divided into an upper column 100a and a lower column 100b arranged vertically which are connected detachably to each other via a connecting member 100c similar to the connecting member 30 described above. In the first column 10 in this case, the upper column 100a is packed with sulfuric acid silica gel to form the upper layer 14 and the lower column 100b is packed with silver nitrate silica gel to form the lower layer 15. When the first column 10 thus constituted is used to extract PCBs from an oily liquid, the upper column 100a only is heated with the first heating unit 40.

(2) In the embodiment described above, the aliphatic hydrocarbon solvent passed through the upper layer 14 consisting of the sulfuric acid silica gel layer is supplied to, and passed through, the lower layer 15 made of the silver nitrate silica gel. Alternatively, the aliphatic hydrocarbon solvent passed through the upper layer 14, before being supplied to the lower layer 15, may be supplied to and passed through a metal salt hydrate silica gel layer.

Figure 7:
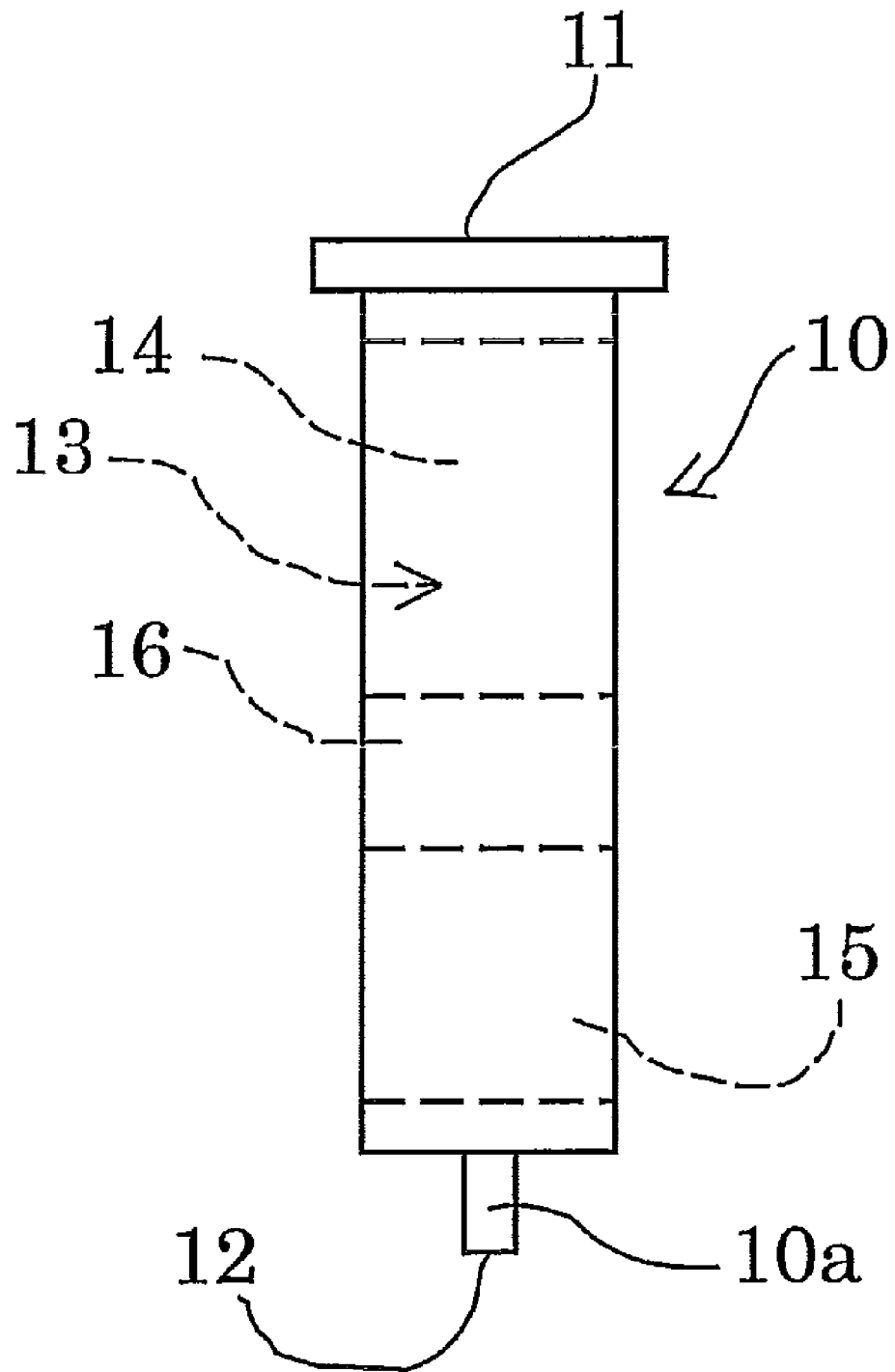
FIG. 7 is a partial schematic diagram showing still another example of the column utilizable in the method for extracting PCBs in the present invention.

This can be achieved for example by arranging an intermediate layer 16 made of a metal salt hydrate silica gel between the upper layer 14 and the lower layer 15, as shown in FIG. 7, in the multilayer silica gel 13 in the first column 10.

The metal salt hydrate silica gel used in the intermediate layer 16 can be prepared by adding an aqueous solution of a metal salt hydrate uniformly to the surface of silica gel and then removing water by heating under reduced pressure. The metal salt hydrate used herein is a metal salt compound having hydration water and includes, for example, copper sulfate hydrates such as copper sulfate pentahydrate, copper nitrate hydrates such as copper nitrate trihydrate, calcium nitrate hydrates such as calcium nitrate tetrahydrate, and iron (III) nitrate hydrates such as iron (III) nitrate nonahydrate. Among them, copper salt hydrates such as copper sulfate pentahydrate and copper nitrate trihydrate are preferable.

Usually, the bulk density of the metal salt hydrate silica gel in the intermediate layer 16 is preferably set at 0.3 to 0.8 g/cm$^3$, more preferably 0.4 to 0.7 g/cm$^3$. When this bulk density is lower than 0.3 g/cm$^3$, the result attained by using the metal salt hydrate silica gel, which will be described later, may be hardly obtained. On the other hand, when the bulk density is higher than 0.8 g/cm$^3$, the rate of chromatographic development of PCBs in the intermediate layer 16 is decreased, and thus a large amount of the aliphatic hydrocarbon solvent may be necessary in the extraction operation described above.

The amount of the metal salt hydrate silica gel used in the intermediate layer 16 is set at a weight ratio of 0.3 to 4.0, more preferably 0.5 to 2.5, relative to the silver nitrate silica gel forming the lower layer 15. When the weight ratio of the metal salt hydrate silica gel is lower than 0.3, the result attained by using the metal salt hydrate silica gel, which will be described later, may be hardly obtained. On the other hand, when the weight ratio is higher than 4.0, the rate of chromatographic development of PCBs in the intermediate layer 16 is decreased, and thus a large amount of the aliphatic hydrocarbon solvent may be necessary in the extraction operation described above.

When the first column 10 containing the intermediate layer 16 is used, the aliphatic hydrocarbon solvent passed through the upper layer 14 consisting of the sulfuric acid silica gel layer 14 is supplied to the intermediate layer 16, passed through the intermediate layer 16, and supplied to the lower layer 15 made of the silver nitrate silica gel. Then, a part of impurity components, particularly electron-donating substances, contained in the aliphatic hydrocarbon solvent from the upper layer 14 are removed by binding to the metal salt hydrate silica gel in the intermediate layer 16. Electron-donating substances contained in the aliphatic hydrocarbon solvent from the upper layer 14 are bound to the silver nitrate silica gel, thereby sometimes forming an adsorbent of PCBs having a small number of chlorine atoms (also referred to hereinafter as "low-chlorinated PCBs"), particularly PCBs having 2 chlorine atoms (also referred to hereinafter as "dichlorinated PCBs"). When the lower layer 15 made of the silver nitrate silica gel in which such an adsorbent is formed is supplied successively with the PCB-containing aliphatic hydrocarbon solvent from the upper layer 14, low-chlorinated PCBs contained in the aliphatic hydrocarbon solvent are adsorbed into the lower layer 15 and removed from the aliphatic hydrocarbon solvent, so that the extraction rate (recovery rate) of low-chlorinated PCBs may be lowered.

In this modified example, electron-donating substances contained in the aliphatic hydrocarbon solvent from the upper layer 14 are removed by the intermediate layer 16 made of the metal salt hydrate silica gel, so that formation of an adsorbent of low-chlorinated PCBs in the lower layer 15 made of the silver nitrate silica gel can be suppressed. PCBs including low-chlorinated PCBs, contained in the aliphatic hydrocarbon solvent from the upper layer 14, are thereby passed through the lower layer 15 made of the silver nitrate silica gel and supplied stably to the alumina layer 23 in the second column 20. Accordingly, when the intermediate layer 16 made of the metal salt hydrate silica gel is used, the extraction rate (recovery rate) of low-chlorinated PCBs, particularly the extraction rate (recovery rate) of dichlorinated PCBs, can be increased, and the extraction rate (recovery rate) of whole PCBs contained in the oily liquid, particularly in the electric insulating oil, can be increased.

Figure 8:
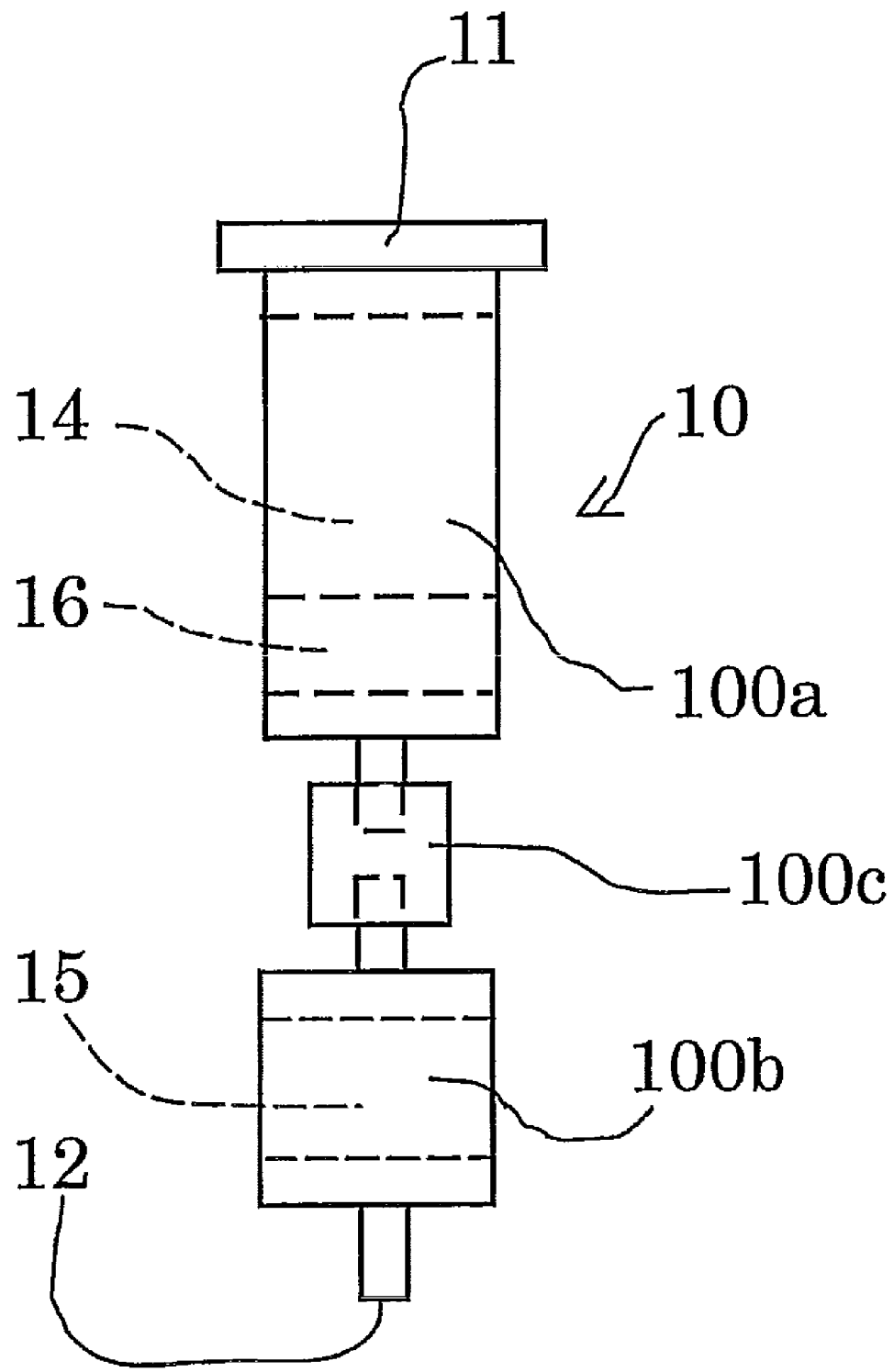
FIG. 8 is a partial schematic diagram showing still another example of the column utilizable in the method for extracting PCBs in the present invention.

This modified example has been described with reference to the example where the first column 10 is composed of a single column in which the upper layer 14, the intermediate layer 16 and the lower layer 15 are stacked as a multilayer. However, the first column 10 having the intermediate layer 16 can be modified. As shown in FIG. 8, the first column 10 may be divided for example into an upper column 100a and a lower column 100b arranged vertically which are connected detachably to each other via a connecting member 100c similar to the connecting member 30 described above. In the first column 10 in this case, the upper column 100a forms a multilayer in which an upper layer 14 packed with the sulfuric acid silica gel and an intermediate layer 16 packed with the metal salt hydrate silica gel are stacked, and the lower column 100b forms a lower layer 15 packed with the silver nitrate silica gel. When the first column 10 is used to extract PCBs from an oily liquid, only the upper layer 14 in the upper column 100a is heated with the first heating unit 40.

Figure 9:
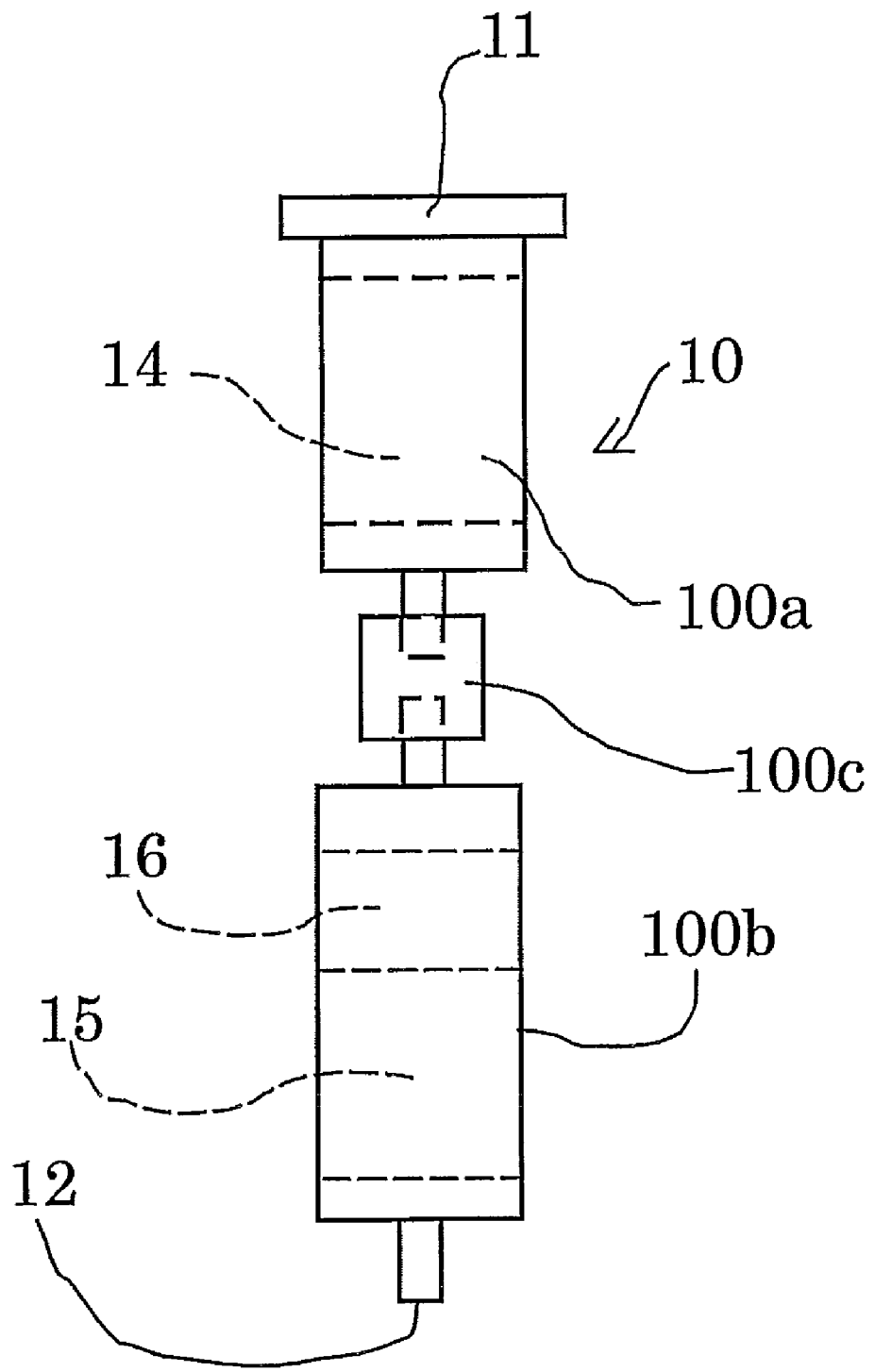
FIG. 9 is a partial schematic diagram showing still another example of the column utilizable in the method for extracting PCBs in the present invention.

In the first column 10 in this modified example, as shown in FIG. 9, only an upper layer 14 packed with the sulfuric acid silica gel is formed in the upper column 100a, and an intermediate layer 16 packed with the metal salt hydrate silica gel and a lower layer 15 packed with the silver nitrate silica gel can be formed as a multilayer in the lower column 100b.

Figure 10:
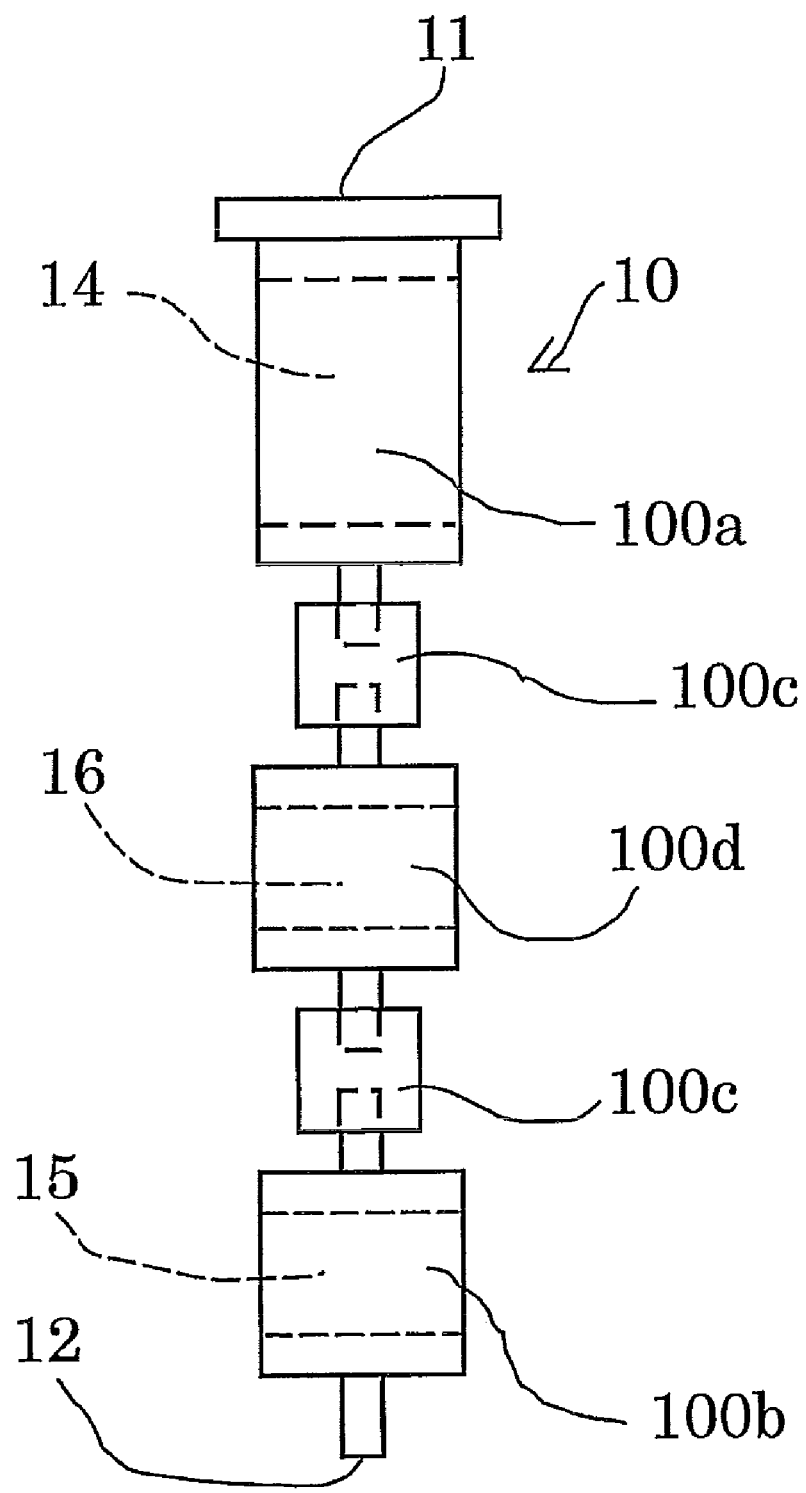
FIG. 10 is a partial schematic diagram showing still another example of the column utilizable in the method for extracting PCBs in the present invention.

The first column 10 that can be used in this modified example may be divided, as shown in FIG. 10, into three vertically arranged columns, that is, an upper column 100a, a middle column 100d and a lower column 100b which are connected detachably between the upper column 100a and the middle column 100d and between the middle column 100d and the lower column 100b via a connecting member 100c similar to the connecting member 30 described above. In the first column 10 in this case, the upper column 100a is packed with the sulfuric acid silica gel to form an upper layer 14, the middle column 100d is packed with the metal salt hydrate silica gel to form an intermediate layer 16, and the lower column 100b is packed with the silver nitrate silica gel to form a lower layer 15. When the first column 10 of this modified example is used to extract PCBs from an oily liquid, the upper column 100a only is heated with the first heating unit 40.

(3) In the embodiments described above, particularly in the above modified example (2), the aliphatic hydrocarbon solvent passed through the sulfuric acid silica gel layer can be supplied to and passed through a carbon material layer, in the process until the aliphatic hydrocarbon solvent is supplied to the alumina layer.

This can be achieved by arranging, in the first column 10 in the column 1, a carbon material layer between the upper layer 14 made of the sulfuric acid silica gel and the lower layer 15 made of the silver nitrate silica gel or between the lower layer 15 and the alumina layer 23. When the first column 10 has an intermediate layer 16 made of the metal salt hydrate silica gel, a carbon material layer can be arranged in an arbitrary position from the upper layer 14 to the lower end 10a of the first column 10. That is, the carbon material layer can be arranged between the upper layer 14 and the intermediate layer 16 or between the intermediate layer 16 and the lower layer 15, or at the lower end 10a side of the lower layer 15. For easily attaining the result described later, however, the carbon material layer is arranged preferably in a position near the upper layer 14.

Figure 11:
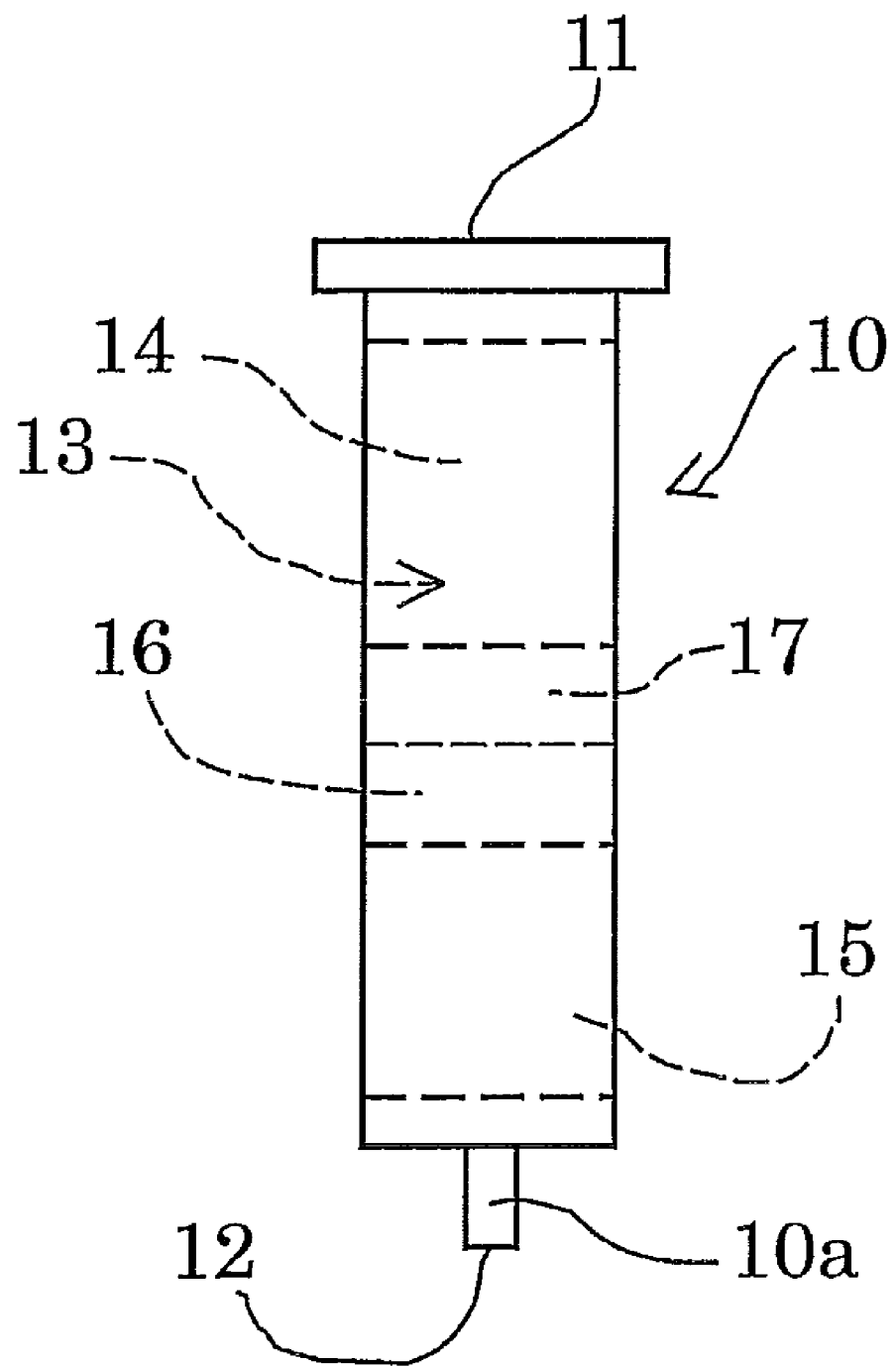
FIG. 11 is a partial schematic diagram showing still another example of the column utilizable in the method for extracting PCBs in the present invention.
Figure 12:
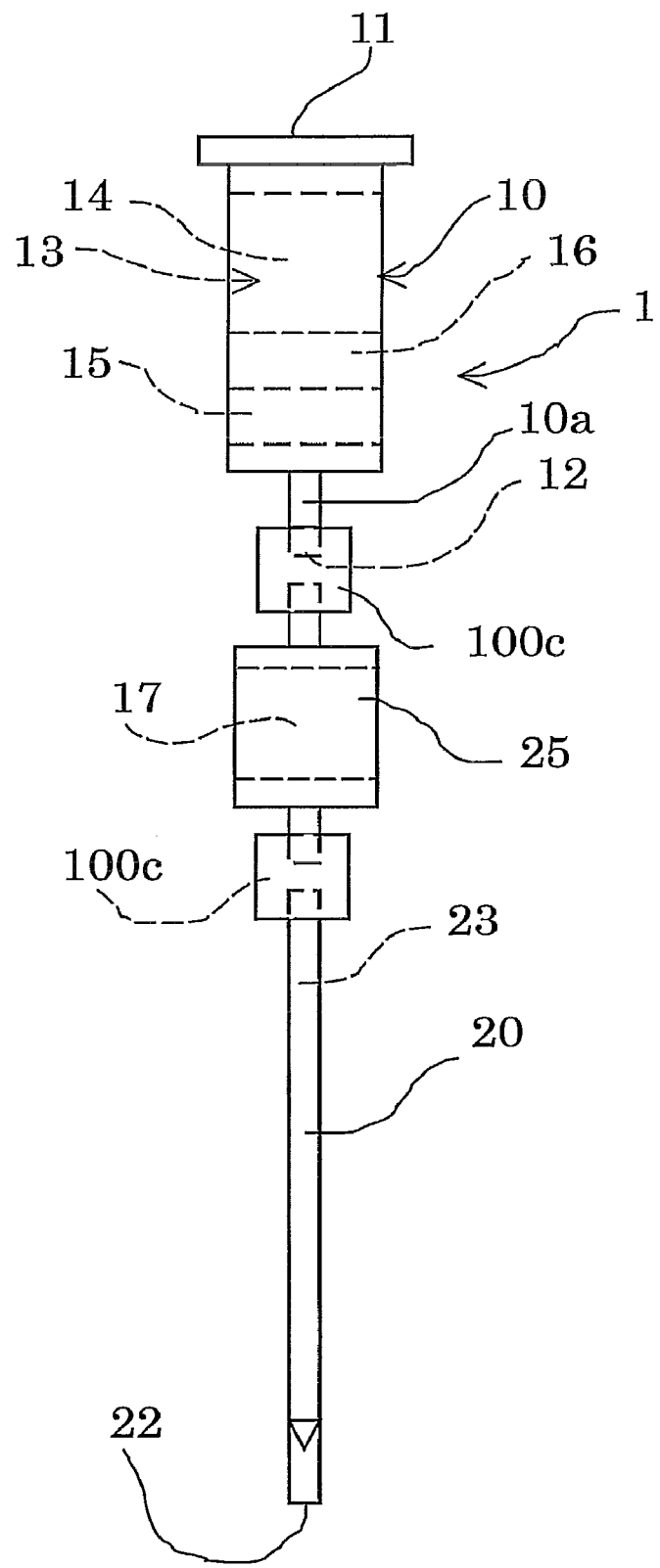
FIG. 12 is a schematic diagram showing still another example of the column utilizable in the method for extracting PCBs in the present invention.

As shown in FIG. 11, one preferable example of the column 1 provided with a carbon material layer is one wherein the multilayer silica gel 13 in the first column 10 consisting of a single column is provided with a carbon material layer 17 between an upper layer 14 and an intermediate layer 16. Another preferable example of the column 1 provided with a carbon material layer, as shown in FIG. 12, is one including a first column 10 consisting of a single column and packed with an upper layer 14, an intermediate layer 16 and a lower layer 15 that are stacked as a multilayer, a second column 20 packed with an alumina layer 23, and a third column 25 packed with a carbon material layer 17, wherein the third column 25 is arranged between the end, at the side of the lower layer 15, of the first column 10 and one end of the second column 20. The third column 25 is connected at one end to the end, at the side of the lower layer 15, of the first column 10 via a connecting member 100c similar to the connecting member 30 described above and also connected at the other end to one end of the second column 20 via a similar connecting member 100c.

A carbon material forming the carbon material layer used in this modified example is active carbon or graphite, preferably in the form of granules to increase the contact area thereof with the aliphatic hydrocarbon solvent passed through the carbon material layer.

The oily liquid containing PCBs may be contaminated with polychlorinated naphthalenes (PCNs) that resemble PCBs in structure and molecular weight. PCNs together with PCBs are dissolved in the aliphatic hydrocarbon solvent, then passed through the upper layer 14 and the lower layer 15 and through the intermediate layer 16 if any and captured by the alumina layer 23 and may, together with PCBs, be extracted with a hydrophobic solvent supplied to, and passed through, the alumina layer 23. Accordingly, PCNs can prevent the extraction of PCBs with high purity from the oily liquid. When an oily liquid is applied to the extraction method in this modified example having a step wherein an aliphatic hydrocarbon solvent is supplied to and passed through the carbon material layer, the carbon material layer selectively captures PCNs from the aliphatic hydrocarbon solvent in which PCBs and PCNs are dissolved, thereby separating the PCNs from the aliphatic hydrocarbon solvent. Accordingly, the extraction method in this modified example using the carbon material layer can extract PCBs with high purity even if the oily liquid contains PCNs together with PCBs.

Typical examples of the oily liquid containing PCNs together with PCBs include the electric insulating oils described above. Before PCBs were added to electric insulating oils for the purpose of increasing electric insulating properties, there was a time when PCNs were added to the oils for the same purpose. At the time when PCBs were used, there was also the circumstance where PCBs were also added to electric insulating oils containing PCNs. Accordingly, there is a high possibility that electric insulating oils that have been long stored for disposal contain PCNs together with PCBs. The extraction method in this modified example is particularly effective in extracting PCBs from the electric insulating oils.

(4) The first column 10 or the like, used in the embodiments described above, in which the upper layer 14 and the lower layer 15 and the intermediate layer 16 and the carbon material layer 17 if any have been stacked may be provided between adjacent layers with a layer made of usual silica gel, a glass layer stable to PCBs and aliphatic hydrocarbon solvents, or a layer of a flocculating material made of solvent- and heat-resistant plastics or the like. The layer of a flocculating material can also be arranged above the upper layer 14, below the lower layer 15 or below the carbon material layer 17.

(5) In the embodiments described above, the columns such as the first column 10 and the second column 20 are connected to each other detachably via the connecting member 30 or the connecting member 100c, but may be connected with another means. For example, the columns may be provided in connecting portions with fitting parts with which the columns can be connected detachably to each other.

(6) In the embodiments described above, the suction unit 50 is arranged in the lower end of the second column 20, and by suction with the suction unit 50, an aliphatic hydrocarbon solvent stored in the first reservoir 60 is supplied to the first column 10. Alternatively, the aliphatic hydrocarbon solvent in the first reservoir 60 may drop naturally into the first column 10 without using the suction unit 50. The aliphatic hydrocarbon solvent can also be supplied to the first column 10 with a metering pump such as a syringe pump or with a pressure device. Alternatively, the aliphatic hydrocarbon solvent may be supplied to the first column 10 by hand with a feeding device such as a pipette.

(7) In the embodiments described above, the hydrophobic solvent supplied to the second reservoir 80 is supplied naturally by its own weight to the second column 20. Alternatively, the hydrophobic solvent can be supplied to the second column 20 with a metering pump such as a syringe pump or with a pressure device.

(8) In the embodiments described above, the second column 20 is separated from the first column 10 when the second column 20 is supplied with an inert gas or a hydrophobic solvent. Alternatively, without separating the second column 20 from the first column 10, the second column 20 can be established so as to be supplied with an inert gas or a hydrophobic solvent. This can be realized by connecting the first column 10 to the second column 20 by a connecting device having a flow path-switching valve. The flow path-switching valve used in this case has an opening for introducing an inert gas, an opening for discharging a hydrophobic solvent, a flow path for connecting the first column 10 and the second column 20, a flow path through which the opening for introducing an inert gas and the second column 20 communicate with each other, and a flow path through which the second column 20 and the opening for discharging a hydrophobic solvent communicate with each other. By switching among the flow paths, it is possible to select any one of the followings: supply of an aliphatic hydrocarbon solvent from the first column 10 to the second column 20, introduction of an inert gas from the opening for introducing an inert gas to the second column 20, and discharge, through the discharging opening, of a hydrophobic solvent supplied to the second column.

(9) In the embodiments described above, the extraction method of the present invention has been described by referring mainly to those cases wherein PCBs are extracted from a sample collected from an oily liquid such as an electric insulating oil in order to determine the concentration of PCBs contained in the oily liquid. However, the present invention can be used for other purposes. For example, an oily liquid containing PCBs should be disposed of after detoxification of PCBs by decomposition, but when a large amount of the oily liquid should be disposed of, such detoxification treatment may be hardly smoothly advanced. Hence, when the extraction method of the present invention is applied to an electric insulating oil to be disposed of, PCBs contained in the oily liquid can be converted into a small amount of a solution in a hydrophobic solvent, thus facilitating the detoxification treatment of PCBs.

Hereinafter, the present invention will be described in more detail with reference to the examples.

Electric insulating oils A, B, C and D used in the examples and comparative examples below are as follows. Among these oils, the electric insulating oils A, B and C were confirmed to be substantially free of PCNs in analysis by GC/ECD, and the electric insulating oil D was confirmed to contain PCNs in analysis by GC/ECD. The concentration of PCNs in the electric insulating oil D is about 24 mg/kg in terms of the concentration of PCBs and is very high as compared with the concentration of coexisting PCBs.

(Electric Insulating Oil A)

This oil was prepared by adding equal amounts of 4 kinds of PCB standards (trade names: Kanechlor Kit KC-300, Kanechlor Kit KC-400, Kanechlor Kit KC-500 and Kanechlor Kit KC-600, manufactured by GL Sciences, Inc.) to a commercial electric insulating oil (trade name: JOMO HS Trans N, manufactured by Japan Energy Corporation) such that the total concentration of PCBs reached 0.42 mg/kg.

(Electric Insulating Oil B)

This oil was prepared by adding equal amounts of 4 kinds of PCB standards (trade names: Kanechlor Kit KC-300, Kanechlor Kit KC-400, Kanechlor Kit KC-500 and Kanechlor Kit KC-600, manufactured by GL Sciences, Inc.) to a PCB-free electric insulating oil removed from a used transformer such that the total concentration of PCBs reached 0.42 mg/kg.

(Electric Insulating Oil C)

This oil is a PCBs-containing electric insulating oil removed from a used transformer.

(Electric Insulating Oil D)

This oil is a PCBs- and PCNs-containing electric insulating oil removed from a used transformer.

EXAMPLE I

The first and second columns used in the following Examples 1 to 14 and Comparative Examples 1 to 6 are as follows.

(First Column)

This column was prepared by charging 0.6 g of silver nitrate silica gel to a height of 10 mm in a column of 13 mm in inner diameter and 50 mm in length and then charging 3.5 g of sulfuric acid silica gel to a height of 40 mm thereon.

(Second Column)

This column was prepared by charging 0.5 g of alumina (trade name: MP Alumina B-Super I, manufactured by MP Bio Medicals) in a column of 2.5 mm in inner diameter and 100 mm in length.

Example 1

85 mg of the electric insulating oil A and 50 µL of an internal standard substance solution for concentration calculation were added to the upper end of the first column allowed to stand such that the sulfuric acid silica gel layer became an upper layer. The sulfuric acid silica gel layer in this first column was heated at 80° C. for 30 minutes and cooled to room temperature, and then the second column was connected to the lower end of the first column. Then, 20 mL of n-hexane was supplied at a rate of 1 mL/min. to the upper end of the first column and then discharged from the lower end of the second column. After supply of n-hexane, the second column was detached from the first column, and n-hexane remaining in the second column was removed. Here, the second column was supplied with a nitrogen gas, while the second column was heated at 80° C.

Next, the second column was supplied at room temperature (20° C.) with toluene in a direction opposite to the direction in which n-hexane was passed, so that PCBs captured by the second column were extracted. Here, the rate of toluene supplied was set at 50 µL/min., and 340 µL of an initial eluate discharged from the second column was collected as an extract of PCBs. The time taken to obtain this extract after initiation of the operation was about 2.2 hours.

The collected extract was measured for its concentration of PCBs. Here, 50 µL of an internal standard substance solution for recovery rate calculation was added to the extract, to prepare an analytical sample. This analytical sample was analyzed by an HRGC/LRMS method in accordance with the method described in "Temporary Manual for Examination of Exogenous Endocrine-Disrupting Chemicals" presented in October, 1998 by the Environment Agency of Japan, and the concentration of PCBs was calculated by a method described in the same manual.

Example 2

85 mg of the electric insulating oil A and 0.40 mL of isooctane were added to the upper end of the first column allowed to stand such that the sulfuric acid silica gel layer became an upper layer. The sulfuric acid silica gel layer in this first column was heated at 80° C. for 30 minutes and cooled to room temperature, and then the second column was connected to the lower end of the first column. Then, 20 mL of n-hexane was supplied at a rate of 1 mL/min. to the upper end of the first column and then discharged from the lower end of the second column. After supply of n-hexane, the second column was detached from the first column, and n-hexane remaining in the second column was removed. Here, the second column was supplied with a nitrogen gas, while the second column was heated at 80° C.

Next, the second column was supplied with toluene in a direction opposite to the direction in which n-hexane was passed, so that PCBs captured by the second column were extracted. Here, the rate of toluene supplied was set at 50 µL/min. while the second column was heated at 80° C., and 170 µL of an initial eluate discharged from the second column was collected as an extract of PCBs. The time taken to obtain this extract after initiation of the operation was about 2 hours.

The collected extract was measured for its concentration of PCBs. Here, the extract was used directly as an analytical sample, and this analytical sample was analyzed by a GC/ECD method in accordance with the method described in Japanese Industrial Standard JIS K 0093 "Testing Methods for Polychlorinated Biphenyl (PCB) in Industrial Water and Waste Water," and the concentration of PCBs was calculated by a method described in the same Japanese Industrial Standard.

Example 3

An extract was obtained in the same manner as in Example 2 except that the electric insulating oil B was used in place of the electric insulating oil A (provided that similar to Example 1, 50 µL of an internal standard substance solution for concentration calculation was added to the upper end of the first column). The time taken to obtain this extract after initiation of the operation was about 2 hours. The collected extract was measured for its concentration of PCBs by the same method as in Example 1.

Example 4

An extract was obtained in the same manner as in Example 2 except that the electric insulating oil B was used in place of the electric insulating oil A. The time taken to obtain this extract after initiation of the operation was about 2 hours. The collected extract was measured for its concentration of PCBs by the same method as in Example 2.

Example 5

An extract was obtained in the same manner as in Example 2 except that the electric insulating oil C was used in place of the electric insulating oil A (provided that similar to Example 1, 50 µL of an internal standard substance solution for concentration calculation was added to the upper end of the first column). The time taken to obtain this extract after initiation of the operation was about 2 hours. The collected extract was measured for its concentration of PCBs by the same method as in Example 1.

Example 6

An extract was obtained in the same manner as in Example 2 except that the electric insulating oil C was used in place of the electric insulating oil A. The time taken to obtain this extract after initiation of the operation was about 2 hours. The collected extract was measured for its concentration of PCBs by the same method as in Example 2.

Example 7

85 mg of the electric insulating oil A, 50 µL of an internal standard substance solution for concentration calculation, and 0.40 mL of isooctane were added to the upper end of the first column allowed to stand such that the sulfuric acid silica gel layer became an upper layer. The sulfuric acid silica gel layer in this first column was heated at 40° C. for 6 hours and cooled to room temperature, and then the second column was connected to the lower end of the first column. Then, 20 mL of n-hexane was supplied at a rate of 1 mL/min. to the upper end of the first column and then discharged from the lower end of the second column. After supply of n-hexane, the second column was detached from the first column, and n-hexane remaining in the second column was removed.

Here, the second column was supplied with a nitrogen gas, while the second column was heated at 80° C.

Next, the second column was supplied with toluene in a direction opposite to the direction in which n-hexane was passed, so that PCBs captured by the second column were extracted. Here, the rate of toluene supplied was set at 50 μL/min. while the second column was heated at 80° C., and 170 μL of an initial eluate discharged from the second column was collected as an extract of PCBs. The time taken to obtain this extract after initiation of the operation was about 7.5 hours.

The collected extract was measured for its concentration of PCBs. Here, 50 μL of an internal standard substance solution for recovery rate calculation was added to the extract, to prepare an analytical sample, and this analytical sample was analyzed by an HRGC/LRMS method in accordance with the method described in "Temporary Manual for Examination of Exogenous Endocrine-Disrupting Chemicals" presented in October, 1998 by the Environment Agency of Japan, and the concentration of PCBs was calculated by a method described in the same manual.

Example 8

An extract of PCBs obtained from the electric insulating oil A in the same manner as in Example 7 (provided that 50 μL of an internal standard substance solution for concentration calculation was not added to the upper end of the first column) was measured for its concentration of PCBs. Here, the extract was used directly as an analytical sample, and this analytical sample was analyzed by a GC/ECD method in accordance with the method described in Japanese Industrial Standard JIS K 0093 "Testing Methods for Polychlorinated Biphenyl (PCB) in Industrial Water and Waste Water," and the concentration of PCBs was calculated by a method described in the same Japanese Industrial Standard.

Example 9

An extract of PCBs was obtained from the electric insulating oil A in the same manner as in Example 7 except that the heating treatment conditions of the sulfuric acid silica gel layer in the first column were changed to 60° C. and 1 hour. The time taken to obtain this extract after initiation of the operation was about 2.5 hours. Then, this extract was measured for its concentration of PCBs by the same method as in Example 7.

Example 10

An extract of PCBs was obtained from the electric insulating oil A in the same manner as in Example 7 (provided that 50 μL of an internal standard substance solution for concentration calculation was not added to the upper end of the first column) except that the heating treatment conditions of the sulfuric acid silica gel layer in the first column were changed to 60° C. and 1 hour. The time taken to obtain this extract after initiation of the operation was about 2.5 hours. Then, this extract was measured for its concentration of PCBs by the same method as in Example 8.

Example 11

An extract of PCBs was obtained from the electric insulating oil A in the same manner as in Example 7 except that isooctane added to the first column was changed to n-hexane, and the heating treatment conditions of the sulfuric acid silica gel layer in the first column were changed to 60° C. and 1 hour. The time taken to obtain this extract after initiation of the operation was about 2.5 hours. Then, this extract was measured for its concentration of PCBs by the same method as in Example 7.

Example 12

An extract of PCBs was obtained from the electric insulating oil A in the same manner as in Example 7 (provided that 50 μL of an internal standard substance solution for concentration calculation was not added to the upper end of the first column) except that isooctane was not added to the first column, the heating treatment conditions of the sulfuric acid silica gel layer in the first column were changed to 60° C. and 1 hour, toluene was supplied to the second column at room temperature without heating the second column, and 340 μL of an initial eluate discharged from the second column was collected as an extract of PCBs. The time taken to obtain this extract after initiation of the operation was about 2.7 hours. Then, this extract was measured for its concentration of PCBs by the same method as in Example 8.

Example 13

An extract of PCBs was obtained from the electric insulating oil A in the same manner as in Example 7 except that the heating treatment conditions of the sulfuric acid silica gel layer in the first column were changed to 80° C. and 30 minutes, the heating temperature of the second column was changed to 40° C., and toluene supplied to the second column was changed to dichloromethane-containing n-hexane (dichloromethane concentration: 20% by volume). The time taken to obtain this extract after initiation of the operation was about 2 hours. Then, this extract was measured for its concentration of PCBs by the same method as in Example 7.

Example 14

An extract of PCBs was obtained from the electric insulating oil A in the same manner as in Example 13 (provided that 50 μL of an internal standard substance solution for concentration calculation was not added to the upper end of the first column). The time taken to obtain this extract after initiation of the operation was about 2 hours. Then, this extract was measured for its concentration of PCBs by the same method as in Example 8.

Comparative Example 1

An analytical sample for concentration of PCBs was prepared from the electric insulating oil A, and the concentration of PCBs in the electric insulating oil A was measured. Here, preparation of the analytical sample and measurement of the concentration of PCBs followed the method described in Appendix No. 2 in Announcement No. 192 issued in 1992 by the Ministry of Health and Welfare of Japan "Method of Testing Standards Concerned with General Waste Subject to Special Control and Industrial Waste Subject to Special Control" (that is, the previously described official method). The time taken to prepare the analytical sample was about 3 days.

Comparative Example 2

In the same manner as in Comparative Example 1, an analytical sample for concentration of PCBs was prepared from the electric insulating oil B, and the concentration of PCBs in the electric insulating oil B was measured. The time taken to prepare the analytical sample was about 3 days.

Comparative Example 3

In the same manner as in Comparative Example 1, an analytical sample for concentration of PCBs was prepared from the electric insulating oil C, and the concentration of PCBs in the electric insulating oil C was measured. The time taken to prepare the analytical sample was about 3 days.

Comparative Example 4

According to the method prescribed in Japanese Industrial Standard JIS K 0311 "Method for Determination of Dioxins in Stationary Source Emissions", the concentration of PCBs in the electric insulating oil A was measured. Specifically, 85 mg of the electric insulating oil A was added to the upper end of a multilayer silica gel column specified by the same measurement method, and n-hexane was supplied at a rate of 2.5 mL/min. to the upper end of this multilayer silica gel column. Then, the whole volume of the n-hexane solution passed through the multilayer silica gel column was collected and concentrated in a rotary evaporator. Next, the whole volume of the concentrated n-hexane solution was added to the upper end of an alumina column specified by the same measurement method, and 10 mL of n-hexane was supplied at a rate of 2.5 mL/min. to the upper end of the alumina column. Subsequently, 60 mL of dichloromethane-containing n-hexane (dichloromethane concentration: 5% by volume) was supplied at a rate of 2.5 mL/min. to the upper end of the alumina column, and the whole volume of the dichloromethane-containing n-hexane solution passed through the alumina column was collected. This dichloromethane-containing n-hexane solution was concentrated in a rotary evaporator, then transferred to a small-quantity concentrating tube, and gently further concentrated while the small-quantity concentrating tube was supplied with a nitrogen stream. The time taken to obtain this concentrate after initiation of the operation was 6 hours.

The concentrate (extract of PCBs) thus obtained was measured for its concentration of PCBs. Here, 50 μL of an internal standard substance solution for recovery rate calculation was added to the concentrate, to prepare an analytical sample. This analytical sample was analyzed by the HRGC/HRMS method in accordance with the same method as in Comparative Example 1, and calculation of the concentration of PCBs was attempted by the method described in the same manual.

Comparative Example 5

An extract of PCBs was obtained from the electric insulating oil A in the same manner as in Example 7 except that the heating conditions of the sulfuric acid silica gel layer in the first column were changed to 20° C. and 8 hours. The time taken to obtain this extract after initiation of the operation was about 9.5 hours. Then, this extract was measured for its concentration of PCBs by the same method as in Example 7.

Comparative Example 6

An extract of PCBs was obtained from the electric insulating oil A in the same manner as in Example 7 (provided that 50 μL of an internal standard substance solution for concentration calculation was not added to the upper end of the first column) except that the heating conditions of the sulfuric acid silica gel layer in the first column were changed to 20° C. and 8 hours. The time taken to obtain this extract after initiation of the operation was about 9.5 hours. Then, this extract was measured for its concentration of PCBs by the same method as in Example 8.

Results of Example I

The extraction conditions and the like in Examples 1 to 14 and Comparative Examples 1 to 6 are collectively shown in Table 1-1 and Table 1-2. The measurement results of concentrations of PCBs in Examples 1 to 14 and Comparative Examples 1 to 6 are shown in Table 2-1 and Table 2-2, and the measurement results of recovery rates of PCBs in some of Examples 1 to 14 and Comparative Examples 1 to 6 are shown in Table 3. The recovery rates of PCBs shown in Table 3 are based on the internal standard substance for concentration calculation and the internal standard substance for recovery rate calculation.

TABLE 1-1

| | | Electric insulating oil | Added solvent (*1) | First column Heating temperature (*2) | Supplied solvent (*3) | Second column Heating temperature (° C.) | Supplied solvent (*4) | Measurement method |
|---|---|---|---|---|---|---|---|---|
| Examples | 1 | A | none | 80 | n-hexane | room temperature | toluene | HRGC/LRMS method |
| | 2 | A | isooctane | 80 | n-hexane | 80 | toluene | GC/ECD method |
| | 3 | B | isooctane | 80 | n-hexane | 80 | toluene | HRGC/LRMS method |
| | 4 | B | isooctane | 80 | n-hexane | 80 | toluene | GC/ECD method |
| | 5 | C | isooctane | 80 | n-hexane | 80 | toluene | HRGC/LRMS method |
| | 6 | C | isooctane | 80 | n-hexane | 80 | toluene | GC/ECD method |
| | 7 | A | isooctane | 40 | n-hexane | 80 | toluene | HRGC/LRMS method |
| | 8 | A | isooctane | 40 | n-hexane | 80 | toluene | GC/ECD method |
| | 9 | A | isooctane | 60 | n-hexane | 80 | toluene | HRGC/LRMS method |
| | 10 | A | isooctane | 60 | n-hexane | 80 | toluene | GC/ECD method |
| | 11 | A | n-hexane | 60 | n-hexane | 80 | toluene | HRGC/LRMS method |
| | 12 | A | none | 60 | n-hexane | room temperature | toluene | GC/ECD method |

TABLE 1-1-continued

| | | | Extraction conditions | | | | |
| --- | --- | --- | --- | --- | --- | --- | --- |
| | | | First column | | | Second column | |
| | Electric insulating oil | Added solvent (*1) | Heating temperature (*2) | Supplied solvent (*3) | Heating temperature (° C.) | Supplied solvent (*4) | Measurement method |
| 13 | A | isooctane | 80 | n-hexane | 40 | mixed solvent (*5) | HRGC/LRMS method |
| 14 | A | isooctane | 80 | n-hexane | 40 | mixed solvent (*5) | GC/ECD method |

(*1): Hydrocarbon solvent added together with an electric insulating oil to the first column
(*2): Heating temperature (° C.) of the sulfuric acid silica gel layer
(*3): Aliphatic hydrocarbon solvent supplied to the first column
(*4): Hydrophobic solvent for extraction of PCBs from the second column
(*5): Dichloromethane-containing n-hexane

TABLE 1-2

| | | | | Extraction conditions | | | | |
| --- | --- | --- | --- | --- | --- | --- | --- | --- |
| | | | | First column | | | Second column | |
| | | Electric insulating oil | Added solvent (*1) | Heating temperature (*2) | Supplied solvent (*3) | Heating temperature (° C.) | Supplied solvent (*4) | Measurement method |
| Comparative Examples | 1 | A | | | official method | | | HRGC/HRMS method |
| | 2 | B | | | official method | | | HRGC/HRMS method |
| | 3 | C | | | official method | | | HRGC/HRMS method |
| | 4 | A | | | JIS K 0311 | | | HRGC/HRMS method |
| | 5 | A | isooctane | 20 | n-hexane | 80 | toluene | HRGC/LRMS method |
| | 6 | A | isooctane | 20 | n-hexane | 80 | toluene | GC/ECD method |

(*1): Hydrocarbon solvent added together with an electric insulating oil to the first column
(*2): Heating temperature (° C.) of the sulfuric acid silica gel layer
(*3): Aliphatic hydrocarbon solvent supplied to the first column
(*4): Hydrophobic solvent for extraction of PCBs from the second column

TABLE 2-1

| | | Concentrations of PCBs (mg/kg) | | | | | | | | | |
| --- | --- | --- | --- | --- | --- | --- | --- | --- | --- | --- | --- |
| | | Homologs | | | | | | | | | Total amount |
| | | $M_1CBs$ | $D_2CBs$ | $T_3CBs$ | $T_4CBs$ | $P_5CBs$ | $H_6CBs$ | $H_7CBs$ | $O_8CBs$ | $N_9CBs$ | $D_{10}CB$ | |
| Examples | 1 | — | N.D. | 0.075 | 0.12 | 0.087 | 0.076 | 0.052 | 0.0079 | — | — | 0.41 |
| | 2 | — | — | — | — | — | — | — | — | — | — | 0.40 |
| | 3 | — | N.D. | 0.072 | 0.11 | 0.087 | 0.073 | 0.052 | 0.0077 | — | — | 0.41 |
| | 4 | — | — | — | — | — | — | — | — | — | — | 0.40 |
| | 5 | — | 0.046 | 0.19 | 0.13 | 0.020 | 0.032 | 0.016 | 0.0048 | — | — | 0.44 |
| | 6 | — | — | — | — | — | — | — | — | — | — | 0.43 |
| | 7 | — | N.D. | 0.081 | 0.12 | 0.086 | 0.078 | 0.051 | 0.0081 | — | — | 0.42 |
| | 8 | — | — | — | — | — | — | — | — | — | — | 0.43 |
| | 9 | — | N.D. | 0.073 | 0.12 | 0.090 | 0.073 | 0.050 | 0.0085 | — | — | 0.41 |
| | 10 | — | — | — | — | — | — | — | — | — | — | 0.42 |

TABLE 2-2

| | | Concentrations of PCBs (mg/kg) | | | | | | | | | |
| --- | --- | --- | --- | --- | --- | --- | --- | --- | --- | --- | --- |
| | | Homologs | | | | | | | | | |
| | | $M_1CBs$ | $D_2CBs$ | $T_3CBs$ | $T_4CBs$ | $P_5CBs$ | $H_6CBs$ | $H_7CBs$ | $O_8CBs$ | $N_9CBs$ | $D_{10}CB$ | Total amount |
| Examples | 11 | — | N.D. | 0.079 | 0.12 | 0.085 | 0.077 | 0.052 | 0.0084 | — | — | 0.42 |
| | 12 | — | — | — | — | — | — | — | — | — | — | 0.43 |

TABLE 2-2-continued

| | | Concentrations of PCBs (mg/kg) | | | | | | | | | |
|---|---|---|---|---|---|---|---|---|---|---|---|
| | | Homologs | | | | | | | | | |
| | | $M_1CBs$ | $D_2CBs$ | $T_3CBs$ | $T_4CBs$ | $P_5CBs$ | $H_6CBs$ | $H_7CBs$ | $O_8CBs$ | $N_9CBs$ | $D_{10}CB$ | Total amount |
| | 13 | — | N.D. | 0.084 | 0.12 | 0.084 | 0.073 | 0.050 | 0.0079 | — | — | 0.42 |
| | 14 | — | — | — | — | — | — | — | — | — | — | 0.43 |
| Comparative | 1 | N.D. | N.D. | 0.077 | 0.12 | 0.085 | 0.064 | 0.049 | 0.0085 | N.D. | N.D. | 0.40 |
| Examples | 2 | N.D. | N.D. | 0.083 | 0.11 | 0.081 | 0.068 | 0.051 | 0.0087 | N.D. | N.D. | 0.41 |
| | 3 | N.D. | 0.048 | 0.20 | 0.13 | 0.018 | 0.030 | 0.017 | 0.0051 | N.D. | N.D. | 0.45 |
| | 4 | | | | | not determinable | | | | | | |
| | 5 | | | | | not determinable | | | | | | |
| | 6 | — | — | — | — | — | — | — | — | — | — | not determinable |

TABLE 3

| | | Recovery rates of PCBs (%) | | | | | | | | |
|---|---|---|---|---|---|---|---|---|---|---|
| | | Homologs | | | | | | | | |
| | | $M_1CBs$ | $D_2CBs$ | $T_3CBs$ | $T_4CBs$ | $P_5CBs$ | $H_6CBs$ | $H_7CBs$ | $O_8CBs$ | $N_9CBs$ | $D_{10}CB$ |
| Examples | 1 | — | 54 | 93 | 95 | 96 | 96 | 97 | 95 | — | — |
| | 3 | — | 53 | 92 | 96 | 98 | 97 | 97 | 95 | — | — |
| | 5 | — | 52 | 91 | 94 | 96 | 92 | 98 | 98 | — | — |
| | 7 | — | 57 | 96 | 97 | 97 | 100 | 98 | 97 | — | — |
| | 9 | — | 52 | 92 | 95 | 96 | 93 | 95 | 92 | — | — |
| | 11 | — | 55 | 93 | 96 | 96 | 94 | 93 | 94 | — | — |
| | 13 | — | 51 | 91 | 95 | 98 | 93 | 98 | 96 | — | — |
| Comparative | 1 | 84 | 93 | 97 | 98 | 97 | 96 | 95 | 96 | 88 | 86 |
| Examples | 2 | 82 | 92 | 95 | 97 | 96 | 95 | 96 | 97 | 89 | 85 |
| | 3 | 84 | 92 | 96 | 94 | 97 | 95 | 93 | 92 | 87 | 85 |
| | 4 | | | | | not determinable | | | | | |
| | 5 | | | | | not determinable | | | | | |

According to Tables 2-1 and 2-2, the concentrations of PCBs in the electric insulating oil A measured in Examples 1, 2 and 7 to 14 agree approximately with the result of Comparative Example 1 where the concentration of PCBs in the electric insulating oil A was measured by the official method. The concentrations of PCBs in the electric insulating oil B measured in Examples 3 and 4 agree approximately with the result of Comparative Example 2 where the concentration of PCBs in the electric insulating oil B was measured by the official method. Further, the concentrations of PCBs in the electric insulating oil C measured in Examples 5 and 6 agree approximately with the result of Comparative Example 3 where the concentration of PCBs in the electric insulating oil C was measured by the official method. Accordingly, the method for extracting PCBs from the respective electric insulating oils in Examples 1 to 14, although the operation is easy and the time taken for treatment is significantly short as compared with the official method, can pretreat the electric insulating oils with the same accuracy as in the official method.

Figure 13:
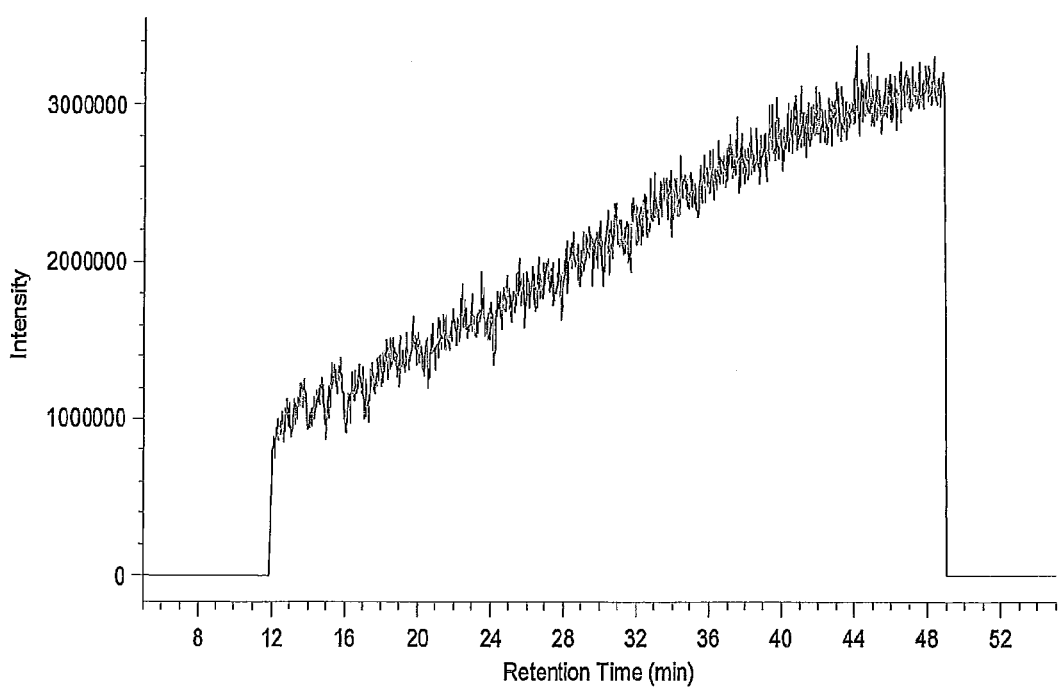
FIG. 13 is a chromatogram in monitor channel of standards for mass calibration, observed in analysis by the HRGC/HRMS method in Comparative Example 4.

Table 2-2 shows that the concentration of PCBs could not be measured in Comparative Example 4. This is because in Comparative Example 4, variations such as waving (rock mass variations) in a chromatogram in monitor channel of the standard for mass calibration are observed in analysis by the HRGC/HRMS method, as shown in FIG. 13, and thus a significant reduction in analytical precision was suspected. The reason that rock mass variations were observed in Comparative Example 4 is that impurity components were not sufficiently removed at the time of extraction of PCBs from the electric insulating oil A. Standards such as JIS K 0311 stipulate that because the pretreatment of a sample is considered insufficient when rock mass variations are observed, the pretreatment of the sample be sufficiently performed again.

Table 2-2 indicates that the concentration of PCBs could not be measured in Comparative Examples 5 and 6. This is because similarly to Comparative Example 4, impurity components were not sufficiently removed at the time of extraction of PCBs from the electric insulating oil A, and thus a significant reduction in analytical precision was suspected in analysis by the HRGC/LRMS method or GC/ECD method.

In Tables 2-1 and 2-2, some of the concentrations of dichlorinated PCBs ($D_2CBs$) that must be contained in the electric insulating oils are indicated by "N.D.", because the content of dichlorinated PCBs in four kinds of PCB standards used in the electric insulating oils A and B was a very small amount and thus lower than the lower detection limit in the HRGC/LRMS method.

EXAMPLE II

The first columns A, B, C and D and the second column used in Examples 15 to 30 and Comparative Examples 7 to 9 below are as follows.

(First Column A)

This column was prepared by charging 0.3 g of silver nitrate silica gel to a height of 5 mm in a column of 13 mm in inner diameter and 55 mm in length, then charging 0.6 g of copper nitrate silica gel to a height of 10 mm thereon and further charging 3.5 g of sulfuric acid silica gel to a height of 40 mm thereon.

The copper nitrate silica gel used herein was prepared in the following manner. 1.0 g of water was added to 3.5 g of copper nitrate trihydrate, thereby sufficiently dissolving it to prepare an aqueous solution. This aqueous solution was added uniformly via a pipette to the surface of 10 g of silica gel and then heated at 70° C. for 2 hours under reduced pressure in a rotary evaporator to remove water. The copper nitrate silica gel thus obtained contains 20% by weight of copper nitrate.
(First Column B)

This column was prepared in the same manner as for the first column A except that copper sulfate silica gel was used in place of copper nitrate silica gel. The copper sulfate silica gel used herein was prepared in the following manner. 10 g of water was added to 4.0 g of copper sulfate pentahydrate, thereby sufficiently dissolving it to prepare an aqueous solution. This aqueous solution was added uniformly via a pipette to the surface of 10 g of silica gel and then heated at 70° C. for 2 hours under reduced pressure in a rotary evaporator to remove water. The copper sulfate silica gel thus obtained contains 20% by weight of copper sulfate.
(First Column C)

This column was prepared in the same manner as for the first column A except that calcium nitrate silica gel was used in place of copper nitrate silica gel. The calcium nitrate silica gel used herein was prepared in the following manner. 2.0 g of water was added to 4.0 g of calcium nitrate tetrahydrate, thereby sufficiently dissolving it to prepare an aqueous solution. This aqueous solution was added uniformly via a pipette to the surface of 10 g of silica gel and then heated at 70° C. for 2 hours under reduced pressure in a rotary evaporator to remove water. The calcium nitrate silica gel thus obtained contains 20% by weight of calcium nitrate.
(First Column D)

This column was prepared in the same manner as for the first column A except that iron (III) nitrate silica gel was used in place of copper nitrate silica gel. The iron (III) nitrate silica gel used herein was prepared in the following manner. 2.0 g of water was added to 6.0 g of iron (III) nitrate nonahydrate, thereby sufficiently dissolving it to prepare an aqueous solution. This aqueous solution was added uniformly via a pipette to the surface of 10 g of silica gel and then heated at 70° C. for 2 hours under reduced pressure in a rotary evaporator to remove water. The iron (III) nitrate silica gel thus obtained contains 26% by weight of iron (III) nitrate.
(Second Column)

This column is the same as used in Example I.

Example 15

85 mg of the electric insulating oil C and 50 µL of an internal standard substance solution for concentration calculation were added to the upper end of the first column A allowed to stand such that the sulfuric acid silica gel layer became an upper layer. The sulfuric acid silica gel layer in this first column A was heated at 80° C. for 30 minutes and cooled to room temperature, and then the second column was connected to the lower end of the first column A. Then, 20 mL of n-hexane was supplied at a rate of 1 mL/min. to the upper end of the first column A and then discharged from the lower end of the second column. After supply of n-hexane, the second column was detached from the first column A, and n-hexane remaining in the second column was removed. Here, the second column was supplied with a nitrogen gas, while the second column was heated at 80° C.

Next, the second column was supplied at room temperature (20° C.) with toluene in a direction opposite to the direction in which n-hexane was passed, so that PCBs captured by the second column were extracted. Here, the rate of toluene supplied was set at 50 µL/min., and 340 µL of an initial eluate discharged from the second column was collected as an extract of PCBs. The time taken to obtain this extract after initiation of the operation was about 2.2 hours.

The collected extract was measured for its concentration of PCBs. Here, 50 µL of an internal standard substance solution for recovery rate calculation was added to the extract, to prepare an analytical sample. This analytical sample was analyzed by an HRGC/LRMS method in accordance with the method described in "Temporary Manual for Examination of Exogenous Endocrine-Disrupting Chemicals" presented in October, 1998 by the Environment Agency of Japan, and the concentration of PCBs was calculated by a method described in the same manual.

Example 16

85 mg of the electric insulating oil C and 0.40 mL of isooctane were added to the upper end of the first column A allowed to stand such that the sulfuric acid silica gel layer became an upper layer. The sulfuric acid silica gel layer in this first column A was heated at 80° C. for 30 minutes and cooled to room temperature, and then the second column was connected to the lower end of the first column A. Then, 20 mL of n-hexane was supplied at a rate of 1 mL/min. to the upper end of the first column A and then discharged from the lower end of the second column. After supply of n-hexane, the second column was detached from the first column A, and n-hexane remaining in the second column was removed. Here, the second column was supplied with a nitrogen gas, while the second column was heated at 80° C.

Next, the second column was supplied with toluene in a direction opposite to the direction in which n-hexane was passed, so that PCBs captured by the second column were extracted. Here, the rate of toluene supplied was set at 50 µL/min. while the second column was heated at 80° C., and 170 µL of an initial eluate discharged from the second column was collected as an extract of PCBs. The time taken to obtain this extract after initiation of the operation was about 2 hours.

The collected extract was measured for its concentration of PCBs. Here, the extract was used directly as an analytical sample, and this analytical sample was analyzed by a GC/ECD method in accordance with the method described in Japanese Industrial Standard JIS K 0093 "Testing Methods for Polychlorinated Biphenyl (PCB) in Industrial Water and Waste Water," and the concentration of PCBs was calculated by a method described in the same Japanese Industrial Standard.

Example 17

85 mg of the electric insulating oil C, 50 µL of an internal standard substance solution for concentration calculation, and 0.40 mL of isooctane were added to the upper end of the first column A allowed to stand such that the sulfuric acid silica gel layer became an upper layer. The sulfuric acid silica gel layer in this first column A was heated at 40° C. for 6 hours and cooled to room temperature, and then the second column was connected to the lower end of the first column A. Then, 20 mL of n-hexane was supplied at a rate of 1 mL/min. to the upper end of the first column A and then discharged from the lower end of the second column. After supply of n-hexane, the second column was detached from the first column A, and n-hexane remaining in the second column was removed. Here, the second column was supplied with a nitrogen gas, while the second column was heated at 80° C.

Next, the second column was supplied with toluene in a direction opposite to the direction in which n-hexane was passed, so that PCBs captured by the second column were extracted. Here, the rate of toluene supplied was set at 50 µL/min. while the second column was heated at 80° C., and 170 µL of an initial eluate discharged from the second column was collected as an extract of PCBs. The time taken to obtain this extract after initiation of the operation was about 7.5 hours.

The collected extract was measured for its concentration of PCBs. Here, 50 µL of an internal standard substance solution for recovery rate calculation was added to the extract, to prepare an analytical sample. This analytical sample was analyzed by an HRGC/LRMS method in accordance with the method described in "Temporary Manual for Examination of Exogenous Endocrine-Disrupting Chemicals" presented in October, 1998 by the Environment Agency of Japan, and the concentration of PCBs was calculated by a method described in the same manual.

Example 18

An extract of PCBs obtained from the electric insulating oil C in the same manner as in Example 17 (provided that 50 µL of an internal standard substance solution for concentration calculation was not added to the upper end of the first column A) was measured for its concentration of PCBs. Here, the extract was used directly as an analytical sample, and this analytical sample was analyzed by a GC/ECD method in accordance with the method described in Japanese Industrial Standard JIS K 0093 "Testing Methods for Polychlorinated Biphenyl (PCB) in Industrial Water and Waste Water", and the concentration of PCBs was calculated by a method described in the same Japanese Industrial Standard.

Example 19

An extract of PCBs was obtained from the electric insulating oil C in the same manner as in Example 17 except that the heating conditions of the sulfuric acid silica gel layer in the first column A were changed to 60° C. and 1 hour. The time taken to obtain this extract after initiation of the operation was about 2.5 hours. Then, this extract was measured for its concentration of PCBs by the same method as in Example 17.

Example 20

An extract of PCBs was obtained from the electric insulating oil C in the same manner as in Example 17 (provided that 50 µL of an internal standard substance solution for concentration calculation was not added to the upper end of the first column B) except that the first column B was used in place of the first column A and the heating conditions of the sulfuric acid silica gel layer therein were changed to 60° C. and 1 hour. The time taken to obtain this extract after initiation of the operation was about 2.5 hours. Then, this extract was measured for its concentration of PCBs by the same method as in Example 18.

Example 21

An extract of PCBs was obtained from the electric insulating oil C in the same manner as in Example 17 except that isooctane added to the first column A was changed to n-hexane and the heating treatment conditions of the sulfuric acid silica gel layer in the first column A were changed to 60° C. and 1 hour. The time taken to obtain this extract after initiation of the operation was about 2.5 hours. Then, this extract was measured for its concentration of PCBs by the same method as in Example 17.

Example 22

An extract of PCBs was obtained from the electric insulating oil C in the same manner as in Example 17 (provided that 50 µL of an internal standard substance solution for concentration calculation was not added to the upper end of the first column A) except that isooctane was not added to the first column A, the heating treatment conditions of the sulfuric acid silica gel layer in the first column A were changed to 60° C. and 1 hour, toluene was added to the second column at room temperature without heating the second column, and 340 µL of an initial eluate discharged from the second column was collected as an extract of PCBs. The time taken to obtain this extract after initiation of the operation was about 2.7 hours. Then, this extract was measured for its concentration of PCBs by the same method as in Example 18.

Example 23

An extract of PCBs was obtained from the electric insulating oil C in the same manner as in Example 17 except that the heating treatment conditions of the sulfuric acid silica gel layer in the first column A were changed to 80° C. and 30 minutes, the heating temperature of the second column was changed to 40° C., and toluene supplied to the second column was changed to dichloromethane-containing n-hexane (dichloromethane concentration: 20% by volume). The time taken to obtain this extract after initiation of the operation was about 2 hours. Then, this extract was measured for its concentration of PCBs by the same method as in Example 17.

Example 24

An extract of PCBs was obtained from the electric insulating oil C in the same manner as in Example 23 (provided that 50 µL of an internal standard substance solution for concentration calculation was not added to the upper end of the first column A). The time taken to obtain this extract after initiation of the operation was about 2 hours. Then, this extract was measured for its concentration of PCBs by the same method as in Example 18.

Example 25

An extract of PCBs was obtained from the electric insulating oil C in the same manner as in Example 17 except that the first column B was used in place of the first column A and the heating conditions of the sulfuric acid silica gel layer therein were changed to 80° C. and 30 minutes. The time taken to obtain this extract after initiation of the operation was about 2 hours. Then, this extract was measured for its concentration of PCBs by the same method as in Example 17.

Example 26

An extract of PCBs was obtained from the electric insulating oil C in the same manner as in Example 25 without adding 50 µL of an internal standard substance solution for concentration calculation to the upper end of the first column B. The time taken to obtain this extract after initiation of the operation was about 2 hours. Then, this extract was measured for its concentration of PCBs by the same method as in Example 18.

Example 27

An extract of PCBs was obtained from the electric insulating oil C in the same manner as in Example 17 except that the first column C was used in place of the first column A and the heating conditions of the sulfuric acid silica gel layer were changed to 80° C. and 30 minutes. The time taken to obtain this extract after initiation of the operation was about 2 hours. Then, this extract was measured for its concentration of PCBs by the same method as in Example 17.

Example 28

An extract of PCBs was obtained from the electric insulating oil C in the same manner as in Example 27 without adding 50 μL of an internal standard substance solution for concentration calculation to the upper end of the first column C. The time taken to obtain this extract after initiation of the operation was about 2 hours. Then, this extract was measured for its concentration of PCBs by the same method as in Example 18.

Example 29

An extract of PCBs was obtained from the electric insulating oil C in the same manner as in Example 17 except that the first column D was used in place of the first column A and the heating conditions of the sulfuric acid silica gel layer were changed to 80° C. and 30 minutes. The time taken to obtain this extract after initiation of the operation was about 2 hours. Then, this extract was measured for its concentration of PCBs by the same method as in Example 17.

Example 30

An extract of PCBs was obtained from the electric insulating oil C in the same manner as in Example 29 without adding 50 μL of an internal standard substance solution for concentration calculation to the upper end of the first column D. The time taken to obtain this extract after initiation of the operation was about 2 hours. Then, this extract was measured for its concentration of PCBs by the same method as in Example 18.

Comparative Example 7

The concentration of PCBs in the electric insulating oil C was measured according to Japanese Industrial Standard JIS K 0311 "Method for Determination of Dioxins in Stationary Source Emissions". Specifically, 85 mg of the electric insulating oil C was added to the upper end of a multilayer silica gel column specified by the same measurement method, and n-hexane was supplied at a rate of 2.5 mL/min. to the upper end of this multilayer silica gel column. Then, the whole volume of the n-hexane solution passed through the multilayer silica gel column was collected and concentrated in a rotary evaporator. Then, the whole volume of the concentrated n-hexane solution was added to the upper end of an alumina column specified by the same measurement method, and 10 mL of n-hexane was supplied at a rate of 2.5 mL/min. to the upper end of the alumina column. Subsequently, 60 mL of dichloromethane-containing n-hexane (dichloromethane concentration: 5% by volume) was supplied at a rate of 2.5 mL/min. to the upper end of the alumina column, and the whole volume of the dichloromethane-containing n-hexane solution passed through the alumina column was collected. This dichloromethane-containing n-hexane solution was concentrated in a rotary evaporator, then transferred to a small-quantity concentrating tube, and gently further concentrated while the small-quantity concentrating tube was supplied with a nitrogen stream. The time taken to obtain this concentrate after initiation of the operation was 6 hours.

The concentrate (extract of PCBs) thus obtained was measured for its concentration of PCBs. Here, 50 μL of an internal standard substance solution for recovery rate calculation was added to the concentrate, to prepare an analytical sample. This analytical sample was analyzed by the HRGC/HRMS method in accordance with the same method as in Comparative Example 1, and calculation of the concentration of PCBs was attempted by the method described in the same manual.

Comparative Example 8

An extract of PCBs was obtained from the electric insulating oil C in the same manner as in Example 17 except that the heating conditions of the sulfuric acid silica gel layer in the first column A were changed to 20° C. and 8 hours. The time taken to obtain this extract after initiation of the operation was about 9.5 hours. Then, this extract was measured for its concentration of PCBs by the same method as in Example 17.

Comparative Example 9

An extract of PCBs was obtained from the electric insulating oil C in the same manner as in Example 17 (provided that 50 μL of an internal standard substance solution for concentration calculation was not added to the upper end of the first column A) except that the heating conditions of the sulfuric acid silica gel layer in the first column A were changed to 20° C. and 8 hours. The time taken to obtain this extract after initiation of the operation was about 9.5 hours. Then, this extract was measured for its concentration of PCBs by the same method as in Example 18.

Results of Example II

The extraction conditions and the like in Examples 15 to 30 and Comparative Examples 7 to 9 are collectively shown in Table 4-1 and Table 4-2. The measurement results of concentrations of PCBs in Examples 15 to 30 and Comparative Examples 7 to 9 are shown in Table 5-1 and Table 5-2, and the measurement results of recovery rates of PCBs in some of Examples 15 to 30 and Comparative Examples 7 to 9 are shown in Table 6. The recovery rates of PCBs shown in Table 6 are based on the internal standard substance for concentration calculation and the internal standard substance for recovery rate calculation. The result of Comparative Example 3 as a comparative example for Examples 15 to 30 is also shown in Table 5-1, Table 5-2 and Table 6.

TABLE 4-1

| | | Electric insulating oil | Extraction conditions | | | | | |
|---|---|---|---|---|---|---|---|---|
| | | | First column | | | | Second column | |
| | | | Type | Added solvent (*1) | Heating temperature (*2) | Supplied solvent (*3) | Heating temperature (° C.) | Supplied solvent (*4) | Measurement method |
| Examples | 15 | C | A | none | 80 | n-hexane | room temperature | toluene | HRGC/LRMS method |

TABLE 4-1-continued

| | | Electric insulating oil | Extraction conditions | | | | | |
|---|---|---|---|---|---|---|---|---|
| | | | First column | | | Second column | | |
| | | | Type | Added solvent (*1) | Heating temperature (*2) | Supplied solvent (*3) | Heating temperature (° C.) | Supplied solvent (*4) | Measurement method |

| | | Electric insulating oil | Type | Added solvent (*1) | Heating temperature (*2) | Supplied solvent (*3) | Heating temperature (° C.) | Supplied solvent (*4) | Measurement method |
|---|---|---|---|---|---|---|---|---|---|
| | 16 | C | A | isooctane | 80 | n-hexane | 80 | toluene | GC/ECD method |
| | 17 | C | A | isooctane | 40 | n-hexane | 80 | toluene | HRGC/LRMS method |
| | 18 | C | A | isooctane | 40 | n-hexane | 80 | toluene | GC/ECD method |
| | 19 | C | A | isooctane | 60 | n-hexane | 80 | toluene | HRGC/LRMS method |
| | 20 | C | B | isooctane | 60 | n-hexane | 80 | toluene | GC/ECD method |
| | 21 | C | A | n-hexane | 60 | n-hexane | 80 | toluene | HRGC/LRMS method |
| | 22 | C | A | none | 60 | n-hexane | room temperature | toluene | GC/ECD method |
| | 23 | C | A | isooctane | 80 | n-hexane | 40 | mixed solvent (*5) | HRGC/LRMS method |
| | 24 | C | A | isooctane | 80 | n-hexane | 40 | mixed solvent (*5) | GC/ECD method |
| | 25 | C | B | isooctane | 80 | n-hexane | 80 | toluene | HRGC/LRMS method |
| | 26 | C | B | isooctane | 80 | n-hexane | 80 | toluene | GC/ECD method |

(*1): Hydrocarbon solvent added together with an electric insulating oil to the first column
(*2): Heating temperature (° C.) of the sulfuric acid silica gel layer
(*3): Aliphatic hydrocarbon solvent supplied to the first column
(*4): Hydrophobic solvent for extraction of PCBs from the second column
(*5): Dichloromethane-containing n-hexane

TABLE 4-2

| | | Electric insulating oil | Type | Added solvent (*1) | Heating temperature (*2) | Supplied solvent (*3) | Heating temperature (° C.) | Supplied solvent (*4) | Measurement method |
|---|---|---|---|---|---|---|---|---|---|
| Examples | 27 | C | C | isooctane | 80 | n-hexane | 80 | toluene | HRGC/LRMS method |
| | 28 | C | C | isooctane | 80 | n-hexane | 80 | toluene | GC/ECD method |
| | 29 | C | D | isooctane | 80 | n-hexane | 80 | toluene | HRGC/LRMS method |
| | 30 | C | D | isooctane | 80 | n-hexane | 80 | toluene | GC/ECD method |
| Comparative Examples | 7 | C | | | JIS K 0311 | | | | HRGC/HRMS method |
| | 8 | C | A | isooctane | 20 | n-hexane | 80 | toluene | HRGC/LRMS method |
| | 9 | C | A | isooctane | 20 | n-hexane | 80 | toluene | GC/ECD method |

(*1): Hydrocarbon solvent added together with an electric insulating oil to the first column
(*2): Heating temperature (° C.) of the sulfuric acid silica gel layer
(*3): Aliphatic hydrocarbon solvent supplied to the first column
(*4): Hydrophobic solvent for extraction of PCBs from the second column

TABLE 5-1

| | | Concentrations of PCBs (mg/kg) | | | | | | | | | |
|---|---|---|---|---|---|---|---|---|---|---|---|
| | | Homologs | | | | | | | | | Total |
| | | $M_1CBs$ | $D_2CBs$ | $T_3CBs$ | $T_4CBs$ | $P_5CBs$ | $H_6CBs$ | $H_7CBs$ | $O_8CBs$ | $N_9CBs$ | $D_{10}CB$ | amount |
| Examples | 15 | — | 0.045 | 0.18 | 0.14 | 0.020 | 0.030 | 0.017 | 0.0050 | — | — | 0.44 |
| | 16 | — | — | — | — | — | — | — | — | — | — | 0.45 |

TABLE 5-1-continued

| | | Concentrations of PCBs (mg/kg) | | | | | | | | | Total amount |
|---|---|---|---|---|---|---|---|---|---|---|---|
| | | Homologs | | | | | | | | | |
| | | $M_1CBs$ | $D_2CBs$ | $T_3CBs$ | $T_4CBs$ | $P_5CBs$ | $H_6CBs$ | $H_7CBs$ | $O_8CBs$ | $N_9CBs$ | $D_{10}CB$ | |
| | 17 | — | 0.047 | 0.19 | 0.13 | 0.018 | 0.032 | 0.017 | 0.0046 | — | — | 0.44 |
| | 18 | — | — | — | — | — | — | — | — | — | — | 0.43 |
| | 19 | — | 0.043 | 0.18 | 0.14 | 0.018 | 0.034 | 0.017 | 0.0045 | — | — | 0.43 |
| | 20 | — | — | — | — | — | — | — | — | — | — | 0.44 |
| | 21 | — | 0.048 | 0.18 | 0.14 | 0.020 | 0.031 | 0.017 | 0.0047 | — | — | 0.44 |
| | 22 | — | — | — | — | — | — | — | — | — | — | 0.45 |
| | 23 | — | 0.049 | 0.20 | 0.14 | 0.019 | 0.033 | 0.017 | 0.0049 | — | — | 0.46 |
| | 24 | — | — | — | — | — | — | — | — | — | — | 0.44 |
| | 25 | — | 0.047 | 0.19 | 0.13 | 0.015 | 0.032 | 0.020 | 0.0045 | — | — | 0.44 |
| | 26 | — | — | — | — | — | — | — | — | — | — | 0.42 |

TABLE 5-2

| | | Concentrations of PCBs (mg/kg) | | | | | | | | | Total amount |
|---|---|---|---|---|---|---|---|---|---|---|---|
| | | Homologs | | | | | | | | | |
| | | $M_1CBs$ | $D_2CBs$ | $T_3CBs$ | $T_4CBs$ | $P_5CBs$ | $H_6CBs$ | $H_7CBs$ | $O_8CBs$ | $N_9CBs$ | $D_{10}CB$ | |
| Examples | 27 | — | 0.050 | 0.22 | 0.11 | 0.016 | 0.028 | 0.019 | 0.0056 | — | — | 0.45 |
| | 28 | — | — | — | — | — | — | — | — | — | — | 0.43 |
| | 29 | — | 0.047 | 0.21 | 0.12 | 0.017 | 0.033 | 0.021 | 0.0053 | — | — | 0.45 |
| | 30 | — | — | — | — | — | — | — | — | — | — | 0.42 |
| Comparative Examples | 3 | N.D. | 0.048 | 0.20 | 0.13 | 0.018 | 0.030 | 0.017 | 0.0051 | N.D. | N.D. | 0.45 |
| | 7 | | | | | | not determinable | | | | | |
| | 8 | | | | | | not determinable | | | | | |
| | 9 | — | — | — | — | — | — | — | — | — | — | not determinable |

TABLE 6

| | | Recovery rates of PCBs (%) | | | | | | | | | |
|---|---|---|---|---|---|---|---|---|---|---|---|
| | | Homologs | | | | | | | | | |
| | | $M_1CBs$ | $D_2CBs$ | $T_3CBs$ | $T_4CBs$ | $P_5CBs$ | $H_6CBs$ | $H_7CBs$ | $O_8CBs$ | $N_9CBs$ | $D_{10}CB$ |
| Examples | 15 | — | 92 | 94 | 95 | 98 | 98 | 100 | 96 | — | — |
| | 17 | — | 95 | 96 | 96 | 91 | 100 | 100 | 95 | — | — |
| | 19 | — | 94 | 92 | 99 | 98 | 101 | 98 | 97 | — | — |
| | 21 | — | 95 | 95 | 102 | 97 | 95 | 94 | 94 | — | — |
| | 23 | — | 92 | 98 | 99 | 99 | 94 | 95 | 94 | — | — |
| | 25 | — | 94 | 94 | 94 | 93 | 98 | 98 | 99 | — | — |
| | 27 | — | 93 | 92 | 93 | 96 | 96 | 97 | 94 | — | — |
| | 29 | — | 90 | 91 | 94 | 95 | 95 | 96 | 97 | — | — |
| Comparative Examples | 3 | 84 | 92 | 96 | 94 | 97 | 95 | 93 | 92 | 87 | 85 |
| | 7 | | | | | Not determinable | | | | | |
| | 8 | | | | | Not determinable | | | | | |

According to Tables 5-1 and 5-2, the concentrations of PCBs in the electric insulating oil C measured in Examples 15 to 30 agree approximately with the result of Comparative Example 3 where the concentration of PCBs in the electric insulating oil C was measured by the official method. Accordingly, the method for extracting PCBs from the electric insulating oil C in Examples 15 to 30, although the operation is easy and the time taken for treatment is significantly short as compared with the official method, can pretreat the electric insulating oil C with the same accuracy as in the official method.

Table 5-2 shows that the concentration of PCBs could not be measured in Comparative Example 7. This is because in Comparative Example 7, impurity components were not sufficiently removed at the time of extraction of PCBs from the electric insulating oil C, and thus rock mass variations similar to those in Comparative Example 4 were observed in analysis by the HRGC/HRMS method, and therefore, a significant reduction in analytical precision was suspected.

Table 5-2 shows that the concentration of PCBs could not be measured in Comparative Examples 8 and 9. This is because similarly to Comparative Example 7, impurity components were not sufficiently removed at the time of extraction of PCBs from the electric insulating oil C, and therefore, a significant reduction in analytical precision was suspected in analysis by the HRGC/LRMS method or GC/ECD method.

According to Tables 2-1, 2-2, 5-1 and 5-2, the concentration of dichlorinated PCBs ($D_2CBs$) could be measured in both Examples I and II. However, comparison between Tables 6 and 3 indicates that the recovery rate of $D_2CBs$ is higher in Example II than in Example I. This is because the first columns A, B, C and D used in Example II have a metal salt hydrate silica gel layer respectively, thus increasing the extraction rate of D₂CBs contained in the electric insulating oil C.

EXAMPLE III

The first columns A, A1, A2 and A3, the first column B1, the first column C1, the first column D1 and the second column used in the following Examples 31 to 42 and Comparative Examples 10 to 13 are as follows. The granular graphite used in the first column is "Envi-Carb 120/400" manufactured by Supelco US.

(First Column A)

This column is the same as the first column A used in Example II.

(First Column A1)

This column was prepared by charging the first column A used in Example II with 0.1 g of granular graphite to a height of 2 mm between sulfuric acid silica gel and copper nitrate silica gel.

(First Column A2)

This column was prepared by charging the first column A used in Example II with 0.1 g of granular graphite to a height of 2 mm between copper nitrate silica gel and silver nitrate silica gel.

(First Column A3)

This column was prepared by charging the first column A used in Example II with 0.1 g of granular graphite to a height of 2 mm below silver nitrate silica gel.

(First Column B1)

This column was prepared by charging the first column B used in Example II with 0.1 g of granular graphite to a height of 2 mm between sulfuric acid silica gel and copper sulfate silica gel.

(First Column C1)

This column was prepared by charging the first column C used in Example II with 0.1 g of granular graphite to a height of 2 mm between sulfuric acid silica gel and calcium nitrate silica gel.

(First Column D1)

This column was prepared by charging the first column D used in Example II with 0.1 g of granular graphite to a height of 2 mm between sulfuric acid silica gel and iron (III) nitrate silica gel.

(Second Column)

This column is the same as used in Example I.

Example 31

85 mg of the electric insulating oil D, 50 µL of an internal standard substance solution for concentration calculation, and 0.40 mL of isooctane were added to the upper end of the first column A1 allowed to stand such that the sulfuric acid silica gel layer became an upper layer. The sulfuric acid silica gel layer in this first column A1 was heated at 80° C. for 30 minutes and cooled to room temperature, and then the second column was connected to the lower end of the first column A1. Then, 20 mL of n-hexane was supplied at a rate of 1 mL/min. to the upper end of the first column A1 and then discharged from the lower end of the second column. After supply of n-hexane, the second column was detached from the first column A1, and n-hexane remaining in the second column was removed. Here, the second column was supplied with a nitrogen gas, while the second column was heated at 80° C.

Next, the second column was supplied with toluene at 80° C. in a direction opposite to the direction in which n-hexane was passed, so that PCBs captured by the second column were extracted. Here, the rate of toluene supplied was set at 50 µL/min., and 170 µL of an initial eluate discharged from the second column was collected as an extract of PCBs. The time taken to obtain this extract after initiation of the operation was about 2 hours.

The collected extract was measured for its concentration of PCBs. Here, 50 µL of an internal standard substance solution for recovery rate calculation was added to the extract, to prepare an analytical sample. This analytical sample was analyzed by an HRGC/LRMS method in accordance with the method described in "Temporary Manual for Examination of Exogenous Endocrine-Disrupting Chemicals" presented in October, 1998 by the Environment Agency of Japan, and the concentration of PCBs was calculated by a method described in the same manual.

Example 32

85 mg of the electric insulating oil D and 0.40 mL of isooctane were added to the upper end of the first column A1 allowed to stand such that the sulfuric acid silica gel layer became an upper layer. The sulfuric acid silica gel layer in this first column A1 was heated at 80° C. for 30 minutes and cooled to room temperature, and then the second column was connected to the lower end of the first column A1. Then, 20 mL of n-hexane was supplied at a rate of 1 mL/min. to the upper end of the first column A1 and then discharged from the lower end of the second column. After supply of n-hexane, the second column was detached from the first column A1, and n-hexane remaining in the second column was removed. Here, the second column was supplied with a nitrogen gas, while the second column was heated at 80° C.

Next, the second column was supplied with toluene in a direction opposite to the direction in which n-hexane was passed, so that PCBs captured by the second column were extracted. Here, the rate of toluene supplied was set at 50 µL/min. while the second column heated at 80° C., and 170 µL of an initial eluate discharged from the second column was collected as an extract of PCBs. The time taken to obtain this extract after initiation of the operation was about 2 hours.

The collected extract was measured for its concentration of PCBs. Here, the extract was used directly as an analytical sample, and this analytical sample was analyzed by a GC/ECD method in accordance with the method described in Japanese Industrial Standard JIS K 0093 "Testing Methods for Polychlorinated Biphenyl (PCB) in Industrial Water and Waste Water", and the concentration of PCBs was calculated by a method described in the same Japanese Industrial Standard.

Example 33

An extract of PCBs was obtained from the electric insulating oil D in the same manner as in Example 32 except that the first column A2 was used in place of the first column A1. The time taken to obtain this extract after initiation of the operation was about 2 hours. Then, this extract was measured for its concentration of PCBs by the same method as in Example 32.

Example 34

An extract of PCBs was obtained from the electric insulating oil D in the same manner as in Example 32 except that the first column A3 was used in place of the first column A1. The time taken to obtain this extract after initiation of the operation was about 2 hours. Then, this extract was measured for its concentration of PCBs by the same method as in Example 32.

Example 35

0.1 g of granular graphite was packed to a height of 55 mm in a glass tube of 2.5 mm in diameter and 60 mm in length sealed at one end with glass wool, and then this glass tube was sealed at the other end with glass wool. One end of this glass tube was connected via a connecting tube to the lower end of the first column A allowed to stand such that the sulfuric acid silica gel layer became an upper layer. Then, 85 mg of the electric insulating oil D and 0.40 mL of isooctane were added to the upper end of the first column A. The sulfuric acid silica gel layer in this first column A was heated at 80° C. for 30 minutes and cooled to room temperature, and then the second column was connected via a connecting tube to the lower end of the glass tube. Then, 20 mL of n-hexane was supplied at a rate of 1 mL/min. to the upper end of the first column A and then discharged from the lower end of the second column. After supply of n-hexane, the second column was detached from the glass tube, and n-hexane remaining in the second column was removed. Here, the second column was supplied with a nitrogen gas, while the second column was heated at 80° C.

Next, the second column was supplied with toluene in a direction opposite to the direction in which n-hexane was passed, so that PCBs captured by the second column were extracted. Here, the rate of toluene supplied was set at 50 µL/min. while the second column was heated at 80° C., and 170 µL of an initial eluate discharged from the second column was collected as an extract of PCBs. The time taken to obtain this extract after initiation of the operation was about 2 hours.

The collected extract was measured for its concentration of PCBs. Here, the extract was used directly as an analytical sample, and this analytical sample was analyzed by a GC/ECD method in accordance with the method described in Japanese Industrial Standard JIS K 0093 "Testing Methods for Polychlorinated Biphenyl (PCB) in Industrial Water and Waste Water", and the concentration of PCBs was calculated by a method described in the same Japanese Industrial Standard.

Example 36

An extract of PCBs was obtained from the electric insulating oil D in the same manner as in Example 32 except that the solvent added to the first column A1 was changed from isooctane to n-hexane and the heating conditions of the sulfuric acid silica gel layer were changed from 80° C. and 30 minutes to 40° C. and 6 hours. The time taken to obtain this extract after initiation of the operation was about 7.5 hours. Then, this extract was measured for its concentration of PCBs by the same method as in Example 32.

Example 37

An extract of PCBs was obtained from the electric insulating oil D in the same manner as in Example 32 except that isooctane was not added to the first column A1 and the heating conditions of the sulfuric acid silica gel layer were changed from 80° C. and 30 minutes to 60° C. and 1 hour. The time taken to obtain this extract after initiation of the operation was about 2.5 hours. Then, this extract was measured for its concentration of PCBs by the same method as in Example 32.

Example 38

An extract of PCBs was obtained from the electric insulating oil D in the same manner as in Example 32 except that the first column B1 was used in place of the first column A1. The time taken to obtain this extract after initiation of the operation was about 2 hours. Then, this extract was measured for its concentration of PCBs by the same method as in Example 32.

Example 39

An extract of PCBs was obtained from the electric insulating oil D in the same manner as in Example 32 except that the first column C1 was used in place of the first column A1. The time taken to obtain this extract after initiation of the operation was about 2 hours. Then, this extract was measured for its concentration of PCBs by the same method as in Example 32.

Example 40

An extract of PCBs was obtained from the electric insulating oil D in the same manner as in Example 32 except that the first column D1 was used in place of the first column A1. The time taken to obtain this extract after initiation of the operation was about 2 hours. Then, this extract was measured for its concentration of PCBs by the same method as in Example 32.

Example 41

An extract of PCBs was obtained from the electric insulating oil C in the same manner as in Example 31 except that the electric insulating oil D was changed to the electric insulating oil C. The time taken to obtain this extract after initiation of the operation was about 2 hours. Then, this extract was measured for its concentration of PCBs by the same method as in Example 31.

Example 42

An extract of PCBs was obtained from the electric insulating oil C in the same manner as in Example 32 except that the electric insulating oil D was changed to the electric insulating oil C. The time taken to obtain this extract after initiation of the operation was about 2 hours. Then, this extract was measured for its concentration of PCBs by the same method as in Example 32.

Comparative Example 10

In the same manner as in Comparative Example 3, a sample for analysis of concentration of PCBs was prepared from the electric insulating oil D. The time taken to prepare the analytical sample was about 3 days. Using this analytical sample, the concentration of PCBs in the electric insulating oil D was measured by the same method as in Comparative Example 3.

Comparative Example 11

The concentration of PCBs in the electric insulating oil D was measured according to Japanese Industrial Standard JIS K 0311 "Method for Determination of Dioxins in Stationary Source Emissions". Specifically, 85 mg of the electric insulating oil D was added to the upper end of a multilayer silica gel column specified by the same measurement method, and n-hexane was supplied at a rate of 2.5 mL/min. to the upper end of this multilayer silica gel column. Then, the whole volume of the n-hexane solution passed through the multilayer silica gel column was collected and concentrated in a rotary evaporator. Then, the whole volume of the concentrated n-hexane solution was added to the upper end of an alumina column specified by the same measurement method, and 10 mL of n-hexane was supplied at a rate of 2.5 mL/min. to the upper end of the alumina column. Subsequently, 60 mL of dichloromethane-containing n-hexane (dichloromethane concentration: 5% by volume) was supplied at a rate of 2.5 mL/min. to the upper end of the alumina column, and the whole volume of the dichloromethane-containing n-hexane solution passed through the alumina column was collected. This dichloromethane-containing n-hexane solution was concentrated in a rotary evaporator, then transferred to a small-quantity concentrating tube, and gently further concentrated while the small-quantity concentrating tube was supplied with a nitrogen stream. The time taken to obtain this concentrate after initiation of the operation was 6 hours.

The concentrate (extract of PCBs) thus obtained was measured for its concentration of PCBs. Here, 50 μL of an internal standard substance solution for recovery rate calculation was added to the concentrate, to prepare an analytical sample. This analytical sample was analyzed by the HRGC/HRMS method in accordance with the same method as in Comparative Example 3, and calculation of the concentration of PCBs was attempted by the method described in the same manual.

Comparative Example 12

An extract of PCBs was obtained from the electric insulating oil D in the same manner as in Example 31 except that the heating conditions of the sulfuric acid silica gel layer in the first column A1 were changed to 20° C. and 8 hours. The time taken to obtain this extract after initiation of the operation was about 9.5 hours. Then, this extract was measured for its concentration of PCBs by the same method as in Example 31.

Comparative Example 13

An extract of PCBs was obtained from the electric insulating oil D in the same manner as in Example 32 except that the heating conditions of the sulfuric acid silica gel layer in the first column A1 were changed to 20° C. and 8 hours. The time taken to obtain this extract after initiation of the operation was about 9.5 hours. Then, this extract was measured for its concentration of PCBs by the same method as in Example 32.

Results of Example III

The extraction conditions and the like in Examples 31 to 42 and Comparative Examples 10 to 13 are collectively shown in Table 7. The measurement results of concentrations of PCBs in Examples 31 to 42 and Comparative Examples 10 to 13 are shown in Table 8-1 and Table 8-2, and the measurement results of recovery rates of PCBs in some of Examples 31 to 42 and Comparative Examples 10 to 13 are shown in Table 9. The recovery rates of PCBs shown in Table 9 are based on the internal standard substance for concentration calculation and the internal standard substance for recovery rate calculation. The result of Comparative Example 3 as a comparative example for Examples 41 and 42 is also shown in Tables 8-2 and 9.

TABLE 7

| | | Electric insulating oil | \multicolumn{4}{c}{Extraction conditions} | | |
| | | | \multicolumn{4}{c}{First column} | \multicolumn{2}{c}{Second column} | |
| | | | Type | Added solvent (*1) | Heating temperature (*2) | Supplied solvent (*3) | Heating temperature (° C.) | Supplied solvent (*4) | Measurement method |
|---|---|---|---|---|---|---|---|---|---|
| Examples | 31 | D | A1 | isooctane | 80 | n-hexane | 80 | toluene | HRGC/LRMS method |
| | 32 | D | A1 | isooctane | 80 | n-hexane | 80 | toluene | GC/ECD method |
| | 33 | D | A2 | isooctane | 80 | n-hexane | 80 | toluene | GC/ECD method |
| | 34 | D | A3 | isooctane | 80 | n-hexane | 80 | toluene | GC/ECD method |
| | 35 | D | A | isooctane | 80 | n-hexane | 80 | toluene | GC/ECD method |
| | 36 | D | A1 | n-hexane | 40 | n-hexane | 80 | toluene | GC/ECD method |
| | 37 | D | A1 | none | 60 | n-hexane | 80 | toluene | GC/ECD method |
| | 38 | D | B1 | isooctane | 80 | n-hexane | 80 | toluene | GC/ECD method |
| | 39 | D | C1 | isooctane | 80 | n-hexane | 80 | toluene | GC/ECD method |
| | 40 | D | D1 | isooctane | 80 | n-hexane | 80 | toluene | GC/ECD method |
| | 41 | C | A1 | isooctane | 80 | n-hexane | 80 | toluene | HRGC/LRMS method |
| | 42 | C | A1 | isooctane | 80 | n-hexane | 80 | toluene | GC/ECD method |
| Comparative Examples | 10 | D | | | \multicolumn{3}{c}{official method} | | | HRGC/HRMS method |
| | 11 | D | | | \multicolumn{3}{c}{JIS K 0311} | | | HRGC/HRMS method |
| | 12 | D | A1 | isooctane | 20 | n-hexane | 80 | toluene | HRGC/LRMS method |
| | 13 | D | A1 | isooctane | 20 | n-hexane | 80 | toluene | GC/ECD method |

(*1): Hydrocarbon solvent added together with an electric insulating oil to the first column
(*2): Heating temperature (° C.) of the sulfuric acid silica gel layer
(*3): Aliphatic hydrocarbon solvent supplied to the first column
(*4): Hydrophobic solvent for extraction of PCBs from the second column

TABLE 8-1

| | | \multicolumn{11}{c}{Concentrations of PCBs (mg/kg)} |
|---|---|---|---|---|---|---|---|---|---|---|---|

| | | | | | | Homologs | | | | | | Total |
|---|---|---|---|---|---|---|---|---|---|---|---|---|
| | | $M_1CBs$ | $D_2CBs$ | $T_3CBs$ | $T_4CBs$ | $P_5CBs$ | $H_6CBs$ | $H_7CBs$ | $O_8CBs$ | $N_9CBs$ | $D_{10}CB$ | amount |
| Examples | 31 | — | N.D. | N.D. | 0.088 | 0.24 | 0.14 | 0.020 | N.D. | — | — | 0.49 |
| | 32 | — | — | — | — | — | — | — | — | — | — | 0.50 |
| | 33 | — | — | — | — | — | — | — | — | — | — | 0.51 |
| | 34 | — | — | — | — | — | — | — | — | — | — | 0.48 |
| | 35 | — | — | — | — | — | — | — | — | — | — | 0.48 |
| | 36 | — | — | — | — | — | — | — | — | — | — | 0.50 |
| | 37 | — | — | — | — | — | — | — | — | — | — | 0.49 |
| | 38 | — | — | — | — | — | — | — | — | — | — | 0.48 |
| | 39 | — | — | — | — | — | — | — | — | — | — | 0.51 |
| | 40 | — | — | — | — | — | — | — | — | — | — | 0.51 |

TABLE 8-2

| | | \multicolumn{11}{c}{Concentrations of PCBs (mg/kg)} |
|---|---|---|---|---|---|---|---|---|---|---|---|

| | | | | | | Homologs | | | | | | |
|---|---|---|---|---|---|---|---|---|---|---|---|---|
| | | $M_1CBs$ | $D_2CBs$ | $T_3CBs$ | $T_4CBs$ | $P_5CBs$ | $H_6CBs$ | $H_7CBs$ | $O_8CBs$ | $N_9CBs$ | $D_{10}CB$ | Total amount |
| Examples | 41 | — | 0.047 | 0.20 | 0.12 | 0.017 | 0.030 | 0.017 | 0.0048 | — | — | 0.44 |
| | 42 | — | — | — | — | — | — | — | — | — | — | 0.44 |
| Comparative | 3 | N.D. | 0.048 | 0.20 | 0.13 | 0.018 | 0.030 | 0.017 | 0.0051 | N.D. | N.D. | 0.45 |
| Examples | 10 | N.D. | N.D. | N.D. | 0.086 | 0.24 | 0.15 | 0.017 | N.D. | N.D. | N.D. | 0.49 |
| | 11 | | | | | | not determinable | | | | | |
| | 12 | | | | | | not determinable | | | | | |
| | 13 | — | — | — | — | — | — | — | — | — | — | not determinable |

TABLE 9

| | | \multicolumn{10}{c}{Recovery rates of PCBs (%)} |
|---|---|---|---|---|---|---|---|---|---|---|---|

| | | \multicolumn{10}{c}{Homologs} |
|---|---|---|---|---|---|---|---|---|---|---|---|
| | | $M_1CBs$ | $D_2CBs$ | $T_3CBs$ | $T_4CBs$ | $P_5CBs$ | $H_6CBs$ | $H_7CBs$ | $O_8CBs$ | $N_9CBs$ | $D_{10}CB$ |
| Examples | 31 | — | 94 | 98 | 96 | 96 | 97 | 98 | 95 | — | — |
| | 41 | — | 93 | 97 | 97 | 95 | 94 | 97 | 96 | — | — |
| Comparative | 3 | 84 | 92 | 96 | 94 | 97 | 95 | 93 | 92 | 87 | 85 |
| Examples | 10 | 82 | 93 | 95 | 93 | 96 | 96 | 95 | 94 | 88 | 82 |
| | 11 | | | | | | not determinable | | | | |
| | 12 | | | | | | not determinable | | | | |

According to Tables 8-1 and 8-2, the concentrations of PCBs in the electric insulating oil D measured in Examples 31 to 40 agree approximately with the result of Comparative Example 10 where the concentration of PCBs in the electric insulating oil D was measured by the official method. Accordingly, the method for extracting PCBs from the electric insulating oil D in Examples 31 to 40, although the electric insulating oil D contains PCNs, can pretreat the electric insulating oil D effectively in a short time.

Table 8-2 shows that the concentration of PCBs could not be measured in Comparative Example 11. This is because in Comparative Example 11, impurity components were not sufficiently removed at the time of extraction of PCBs from the electric insulating oil D, and thus rock mass variations similar to those in Comparative Example 4 were observed in analysis by the HRGC/HRMS method, and therefore, a significant reduction in analytical precision was suspected.

Table 8-2 shows that the concentration of PCBs could not be measured in Comparative Examples 12 and 13. This is because similarly to Comparative Example 7, impurity components were not sufficiently removed at the time of extraction of PCBs from the electric insulating oil D, and therefore, a significant reduction in analytical precision was suspected in analysis by the HRGC/LRMS method or GC/ECD method.

The present invention can be carried out in various other forms without departure from the spirit and major features of the present invention. Accordingly, the embodiments and examples described above are merely illustrative in all aspects and are not to be construed as restrictive. The scope of the present invention is defined by the claims and is not restricted in any sense by the description of the specification. Any variations and modifications that fall within equivalence of the claims are intended to fall within the scope of the present invention.

The invention claimed is:

1. A method for extracting polychlorinated biphenyls from an oily liquid containing polychlorinated biphenyls, comprising the steps of:
   adding the oily liquid to a sulfuric acid silica gel layer,
   allowing the sulfuric acid silica gel layer to which the oily liquid is added to be kept in a state heated to at least 35° C. for a predetermined time and then cooling the layer to ordinary temperature, supplying an aliphatic hydrocarbon solvent to the sulfuric acid silica gel layer cooled to ordinary temperature, allowing the aliphatic hydrocarbon solvent passed through the sulfuric acid silica gel layer to be supplied to, and passed through, a metal salt hydrate silica gel layer, allowing the aliphatic hydrocarbon solvent passed through the metal salt hydrate silica gel layer to be supplied to, and passed through, a silver nitrate silica gel layer, allowing the aliphatic hydrocarbon solvent passed through the silver nitrate silica gel layer to be supplied to, and passed through, an alumina layer, allowing a hydrophobic solvent capable of dissolving the polychlorinated biphenyls to be supplied to, and passed through, the alumina layer, and securing the hydrophobic solvent passed through the alumina layer, wherein a metal salt hydrate silica gel used in the metal salt hydrate silica gel layer is prepared by adding to silica gel an aqueous solution of a metal salt hydrate selected from the group consisting of copper sulfate hydrates, copper nitrate hydrates, calcium nitrate hydrates, and iron nitrate hydrates and then removing water by heating under reduced pressure.

2. The method for extracting polychlorinated biphenyls according to claim 1, wherein the sulfuric acid silica gel layer, the metal salt hydrate silica gel layer and the silver nitrate silica gel layer are stacked and packed in this order in a first column, and the alumina layer is packed in a second column attachable to and detachable from the silver nitrate silica gel layer side of the first column.

3. The method for extracting polychlorinated biphenyls according to claim 2, wherein the hydrophobic solvent is supplied to, and passed through, the alumina layer in a direction opposite to the direction in which the aliphatic hydrocarbon solvent is passed.

4. The method for extracting polychlorinated biphenyls according to claim 1, wherein the aliphatic hydrocarbon solvent is supplied to and passed through a carbon material layer, in the process until the aliphatic hydrocarbon solvent passed through the sulfuric acid silica gel layer is supplied to the alumina layer.

5. The method for extracting polychlorinated biphenyls according to claim 4, wherein the carbon material layer is a layer made of graphite.

6. The method for extracting polychlorinated biphenyls according to claim 4, wherein the oily liquid further comprises polychlorinated naphthalenes.

7. The method for extracting polychlorinated biphenyls according to claim 6, wherein the oily liquid is an electric insulating oil.

8. The method for extracting polychlorinated biphenyls according to claim 1, wherein a hydrocarbon solvent having a boiling point not lower than the heating temperature of the sulfuric acid silica gel layer and being capable of dissolving the oily liquid, together with the oily liquid, is added to the sulfuric acid silica gel layer.

9. The method for extracting polychlorinated biphenyls according to claim 2, which further comprises removing the aliphatic hydrocarbon solvent remaining in the alumina layer, before the hydrophobic solvent is supplied to the alumina layer.

10. The method for extracting polychlorinated biphenyls according to claim 2, wherein the alumina layer is supplied with the hydrophobic solvent while the alumina layer is heated to at least 35° C.

11. A method for measuring polychlorinated biphenyls in a polychlorinated biphenyls-containing oily liquid, comprising the steps of:

adding a sample collected from the oily liquid to a sulfuric acid silica gel layer, allowing the sulfuric acid silica gel layer to which the sample is added to be kept in a state heated to at least 35° C. for a predetermined time and then cooling the layer to ordinary temperature, supplying an aliphatic hydrocarbon solvent to the sulfuric acid silica gel layer cooled to ordinary temperature, allowing the aliphatic hydrocarbon solvent passed through the sulfuric acid silica gel layer to be supplied to, and passed through, a metal salt hydrate silica gel layer, allowing the aliphatic hydrocarbon solvent passed through the metal salt hydrate silica gel layer to be supplied to, and passed through, a silver nitrate silica gel layer, allowing the aliphatic hydrocarbon solvent passed through the silver nitrate silica gel layer to be supplied to, and passed through, an alumina layer, allowing a hydrophobic solvent capable of dissolving the polychlorinated biphenyls to be supplied to, and passed through, the alumina layer, securing the hydrophobic solvent passed through the alumina layer, and analyzing the secured hydrophobic solvent by gas chromatography, wherein a metal salt hydrate silica gel used in the metal salt hydrate silica gel layer is prepared by adding to silica gel an aqueous solution of a metal salt hydrate selected from the group consisting of copper sulfate hydrates, copper nitrate hydrates, calcium nitrate hydrates, and iron nitrate hydrates an then removing water by heating under reduced pressure.

12. The method for measuring polychlorinated biphenyls according to claim 11, wherein the sulfuric acid silica gel layer, the metal salt hydrate silica gel layer and the silver nitrate silica gel layer are stacked and packed in this order in a first column, and the alumina layer is packed in a second column attachable to and detachable from the silver nitrate silica gel layer side of the first column.

13. The method for measuring polychlorinated biphenyls according to claim 12, wherein the hydrophobic solvent is supplied to, and passed through, the alumina layer in a direction opposite to the direction in which the aliphatic hydrocarbon solvent is passed.

14. The method for measuring polychlorinated biphenyls according to claim 11, wherein the aliphatic hydrocarbon solvent is supplied to and passed through a carbon material layer, in the process until the aliphatic hydrocarbon solvent passed through the sulfuric acid silica gel layer is supplied to the alumina layer.

* * * * *